US012678130B2

(12) United States Patent
Shimoyama

(10) Patent No.: US 12,678,130 B2
(45) Date of Patent: Jul. 14, 2026

(54) ENDOSCOPE BALLOON, ENDOSCOPE BALLOON UNIT, AND ENDOSCOPE

(71) Applicant: FUJIFILM Corporation, Tokyo (JP)

(72) Inventor: Yuto Shimoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/829,655

(22) Filed: Sep. 10, 2024

(65) Prior Publication Data

US 2025/0099073 A1    Mar. 27, 2025

(30) Foreign Application Priority Data

Sep. 21, 2023    (JP) ................................. 2023-155555

(51) Int. Cl.
*A61B 8/12*        (2006.01)
*A61B 8/00*        (2006.01)
(52) U.S. Cl.
CPC ................ *A61B 8/12* (2013.01); *A61B 8/445* (2013.01)
(58) Field of Classification Search
CPC ....... A61B 8/12; A61B 8/445; A61B 1/00082; A61B 2017/348; A61B 5/6858
See application file for complete search history.

(56) References Cited

U.S. PATENT DOCUMENTS

| | | | |
|---|---|---|---|
| 2007/0249940 A1* | 10/2007 | Kohno | A61B 1/00098 600/463 |
| 2007/0276181 A1* | 11/2007 | Terliuc | A61B 1/041 600/106 |
| 2017/0014099 A1* | 1/2017 | Morimoto | A61B 1/0008 |
| 2017/0144193 A1* | 5/2017 | Sato | G01N 29/24 |
| 2023/0095773 A1 | 3/2023 | Shimoyama | |

FOREIGN PATENT DOCUMENTS

JP        2023-047488 A    4/2023

* cited by examiner

*Primary Examiner* — Pascal M Bui Pho
*Assistant Examiner* — Michael Yiming Fang
(74) *Attorney, Agent, or Firm* — Studebaker Brackett PLLC

(57) ABSTRACT

Provided are an endoscope balloon with improved fixation to a distal end part body of an endoscope insertion part, an endoscope balloon unit, and an endoscope. An endoscope balloon includes a cover body that has a bottomed tubular shape which is closed on a distal end side and is open on a base end side, includes a bulging portion configured to bulge by storing an ultrasonic transmission medium, and is mounted on a distal end part body and covers an ultrasonic transducer, a fixing body that is provided on the base end side with respect to the cover body and that is fixed to a fixed part of an endoscope insertion part, and a connecting body that connects the cover body and the fixing body.

14 Claims, 22 Drawing Sheets

ENDOSCOPE BALLOON, ENDOSCOPE BALLOON UNIT, AND ENDOSCOPE

CROSS-REFERENCE TO RELATED APPLICATION

The present application claims priority under 35 U.S.C § 119(a) to Japanese Patent Application No. 2023-155555 filed on Sep. 21, 2023, which is hereby expressly incorporated by reference, in its entirety, into the present application.

BACKGROUND OF THE INVENTION

1. Field of the Invention

The present disclosure relates to an endoscope balloon mounted on a distal end part body of an endoscope insertion part, an endoscope balloon unit, and an endoscope.

2. Description of the Related Art

An ultrasonic endoscope includes an ultrasonic transducer disposed in a distal end part body of an endoscope insertion part to be inserted into a body cavity of a subject. The ultrasonic transducer emits an ultrasonic wave toward a site to be observed in the body cavity and receives an echo signal reflected from the site to be observed, and outputs an electric signal corresponding to the received echo signal to an ultrasonic observation device. Then, the electric signal is subjected to various kinds of signal processing in the ultrasonic observation device, and is then displayed on a monitor or the like as an ultrasonic tomographic image.

The ultrasonic wave and the echo signal are considerably attenuated in a case in which air is interposed between the ultrasonic transducer and the site to be observed, so that it is necessary to interpose an ultrasonic transmission medium, such as water or oil, between the ultrasonic transducer and the site to be observed. Therefore, an elastic balloon is mounted on the distal end part body of the endoscope insertion part. In addition, the balloon is inflated by injecting the ultrasonic transmission medium into the balloon and causing the balloon to come into contact with the site to be observed, thereby eliminating air from between the ultrasonic transducer and the site to be observed and preventing the attenuation of the ultrasonic wave and the echo signal.

For example, JP2023-47488A discloses a balloon having a two-layer structure including an inner part and an outer part. With this balloon, since a space defined between the inner part and the outer part serves as a storage part for storing the ultrasonic transmission medium, liquid tightness of the storage part is easily ensured as compared with a balloon having a general configuration in which a space between the distal end part body of the endoscope insertion part and the balloon serves as the storage part.

SUMMARY OF THE INVENTION

The balloon disclosed in JP2023-47488A has a bottomed tubular shape which is closed on a distal end side and is open on a base end side, and is of a type to be mounted by covering the distal end part body with the balloon from the distal end side. However, in this balloon, since two standing wall parts disposed on both sides of the ultrasonic transducer in the distal end part body are fixed to the distal end part body by being held from an outside, there is a problem in that a sufficient fixing force cannot be obtained. In particular, since an inner diameter of a lumen such as a bronchus or a pharynx is narrow, in a case in which the endoscope insertion part is removed from the lumen, a load is applied in a direction in which the balloon turns over due to contact between the balloon and the lumen, and there is a concern that the balloon may come off.

The present invention has been made in view of such circumstances, and an object of the present invention is to provide an endoscope balloon with improved fixation to a distal end part body of an endoscope insertion part, an endoscope balloon unit, and an endoscope.

The present disclosure includes the following aspects.

A first aspect provides an endoscope balloon that covers an ultrasonic transducer provided in a distal end part body of an endoscope insertion part, the endoscope balloon comprising: a cover body that has a bottomed tubular shape which is closed on a distal end side in a first direction corresponding to a longitudinal direction of the endoscope insertion part and which is open on a base end side in the first direction, includes a bulging portion configured to bulge by storing an ultrasonic transmission medium, and is mounted on the distal end part body and covers the ultrasonic transducer; a fixing body that is provided on the base end side with respect to the cover body and that is fixed to a fixed part of the endoscope insertion part; and a connecting body that connects the cover body and the fixing body.

A second aspect provides the endoscope balloon according to the first aspect, in which the fixing body is closely fixed to the fixed part.

A third aspect provides the endoscope balloon according to the first or second aspect, in which the fixing body is configured of a tubular body having a through-passage in the first direction, and an inner peripheral surface of the tubular body is fixed to the fixed part.

A fourth aspect provides the endoscope balloon according to the third aspect, in which the opening of the cover body is provided at a position intersecting an extension direction of an axis of the through-passage.

A fifth aspect provides the endoscope balloon according to any one of the first to fourth aspects, in which the fixing body is fixed to the distal end part body as the fixed part.

A sixth aspect provides the endoscope balloon according to any one of the first to fourth aspects, in which the endoscope insertion part has a bendable part on the base end side of the distal end part body, and the fixing body is fixed to the bendable part as the fixed part.

A seventh aspect provides the endoscope balloon according to any one of the first to sixth aspects, in which the cover body has a cover body fixing portion that is fixed to the distal end part body.

An eighth aspect provides the endoscope balloon according to the seventh aspect, in which the cover body fixing portion has a pair of fixing surfaces facing each other in a second direction orthogonal to the first direction, and the pair of fixing surfaces elastically hold the distal end part body.

A ninth aspect provides the endoscope balloon according to any one of the first to eighth aspects, in which the distal end part body has a treatment tool outlet port, and the connecting body has a gutter shape that is open on a side where the treatment tool outlet port is provided.

A tenth aspect provides the endoscope balloon according to any one of the first to ninth aspects, in which the cover body has an inner part, an outer part that covers the inner part, and a storage part that stores the ultrasonic transmission medium between the inner part and the outer part, and the outer part has the bulging portion at a position facing a transducer surface of the ultrasonic transducer.

An eleventh aspect provides the endoscope balloon according to the tenth aspect, in which the inner part, the connecting body, and the fixing body are integrally formed.

A twelfth aspect provides the endoscope balloon according to the tenth or eleventh aspect, in which the connecting body has a communication port that communicates with the storage part.

A thirteenth aspect provides an endoscope balloon unit comprising: the endoscope balloon according to any one of the first to twelfth aspects; an attachment member that is attachable to and detachable from an operation part connected to the base end side of the endoscope insertion part and has a supply/discharge port for supplying and discharging the ultrasonic transmission medium; and a pipe line member that sends the ultrasonic transmission medium between the attachment member and the endoscope balloon.

A fourteenth aspect provides an endoscope mounted with the endoscope balloon unit according to the thirteenth aspect.

According to the present invention, it is possible to improve the fixation to the distal end part body of the endoscope insertion part.

DESCRIPTION OF THE PREFERRED EMBODIMENTS

Figure 1:
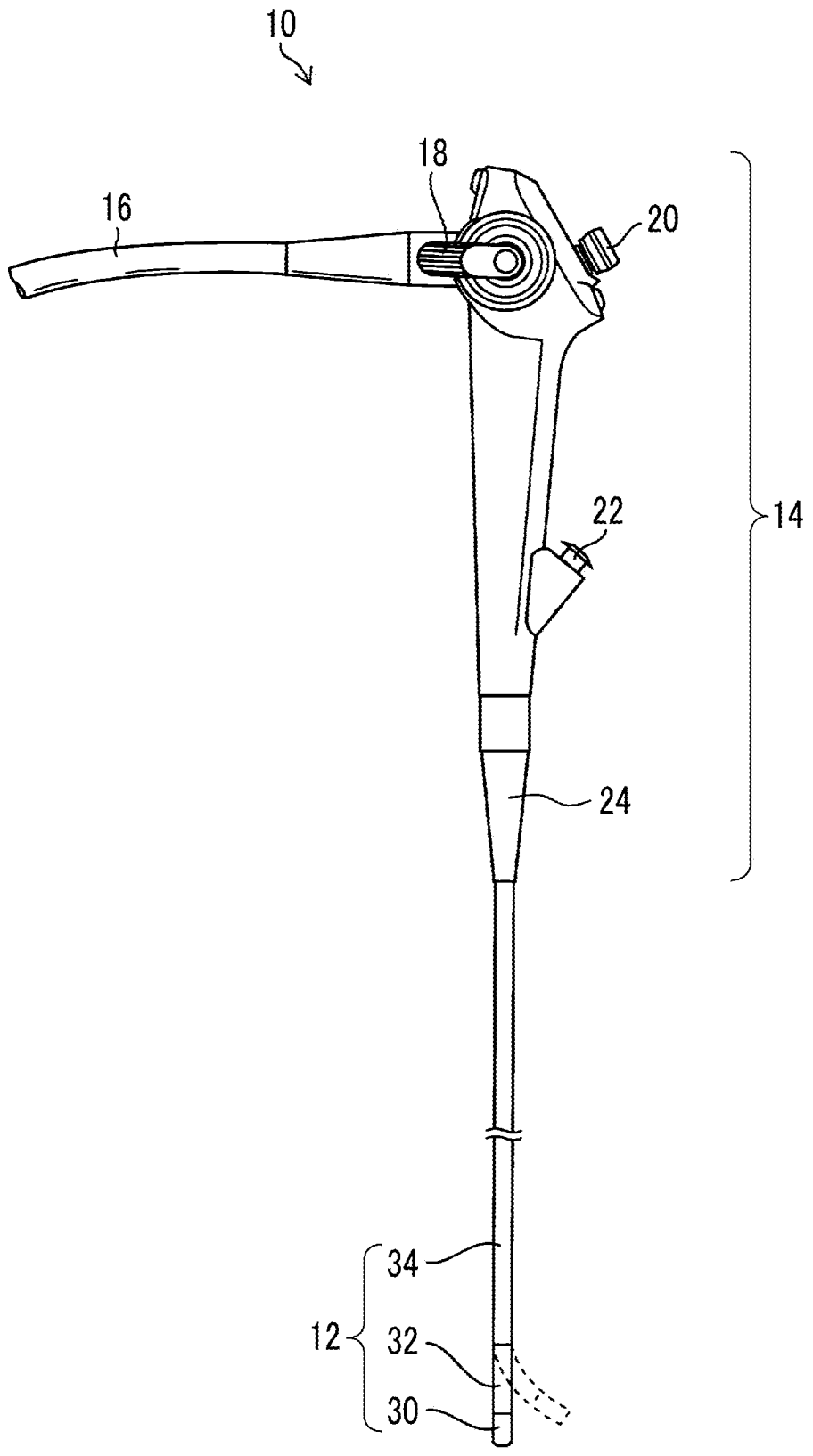
FIG. 1 is a schematic diagram showing a configuration of an endoscope device.

Hereinafter, an embodiment of the present invention will be described with reference to the accompanying drawings.
Ultrasonic Endoscope FIG. 1 is a schematic diagram showing a configuration of an ultrasonic endoscope 10. As shown in FIG. 1, the ultrasonic endoscope 10 (hereinafter, referred to as an "endoscope 10") is an ultrasonic bronchoscope and is used for collecting a cell tissue of a lesion part (which can also be an observation site, an examination site, or a checkup site).

The endoscope 10 comprises an insertion part 12 to be inserted into a body of a patient (hereinafter, referred to as an "endoscope insertion part 12"), an operation part 14 that is installed consecutively to a base end part of the endoscope insertion part 12 and that is gripped by an operator to perform various operations, and a universal cord 16 of which one end is connected to the operation part 14.

The operation part 14 is provided with various operation members that are operated by the operator. For example, an angle lever 18, a suction button 20, and the like are provided.

In addition, the operation part 14 is provided with a treatment tool inlet port 22 into which a treatment tool is inserted. The treatment tool inlet port 22 communicates with a treatment tool insertion channel 62 (see FIG. 3) described below.

Although not shown, the other end part of the universal cord 16 is provided with an ultrasound connector that is connected to an ultrasound processor device, an endoscope connector that is connected to an endoscope processor device, and a light source connector that is connected to a light source device. The endoscope 10 is attachably and detachably connected to the ultrasound processor device, the endoscope processor device, and the light source device via these connectors.

A cylindrical diameter-reduced part 24 that reduces in diameter toward the endoscope insertion part 12 side (distal end side) is provided on a distal end side (side where the endoscope insertion part 12 is provided) of the operation part 14. The endoscope insertion part 12 is installed consecutively on a distal end side of the diameter-reduced part 24, and the diameter-reduced part 24 serves as a bending prevention member. An attachment member 200, which will be described below, is attachably and detachably mounted on the diameter-reduced part 24 of the operation part 14 (see FIGS. 18 and 22).

The endoscope insertion part 12 extends from a distal end of the operation part 14 and is formed in a small-diameter elongated shape as a whole. The endoscope insertion part 12 is configured of a distal end part body 30, a bendable part 32, and a soft part 34 in this order from the distal end side to a base end side. A configuration of the distal end part body 30 will be described below.

The bendable part 32 performs a bending operation in an up-down direction by rotating the angle lever 18 of the operation part 14. The distal end part body 30 can be directed in a desired direction by the bending operation.

The soft part 34 occupies most of the endoscope insertion part 12 and has flexibility to bend in any direction. In a case in which the endoscope insertion part 12 is inserted into a body cavity, the soft part 34 is bent along an insertion path into the body cavity.

Distal End Part Body

Figure 2:
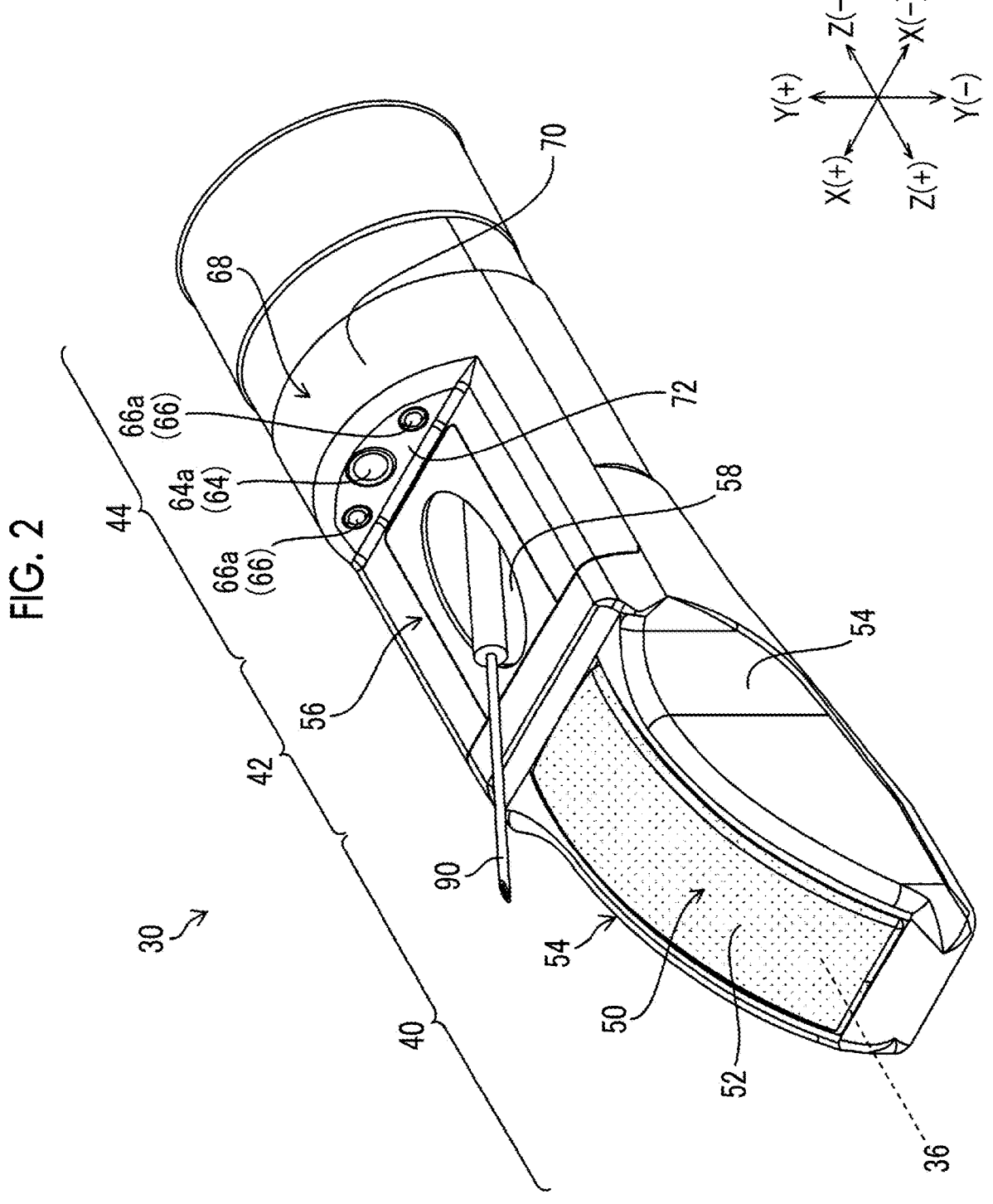
FIG. 2 is a perspective view of a distal end part body.
Figure 3:
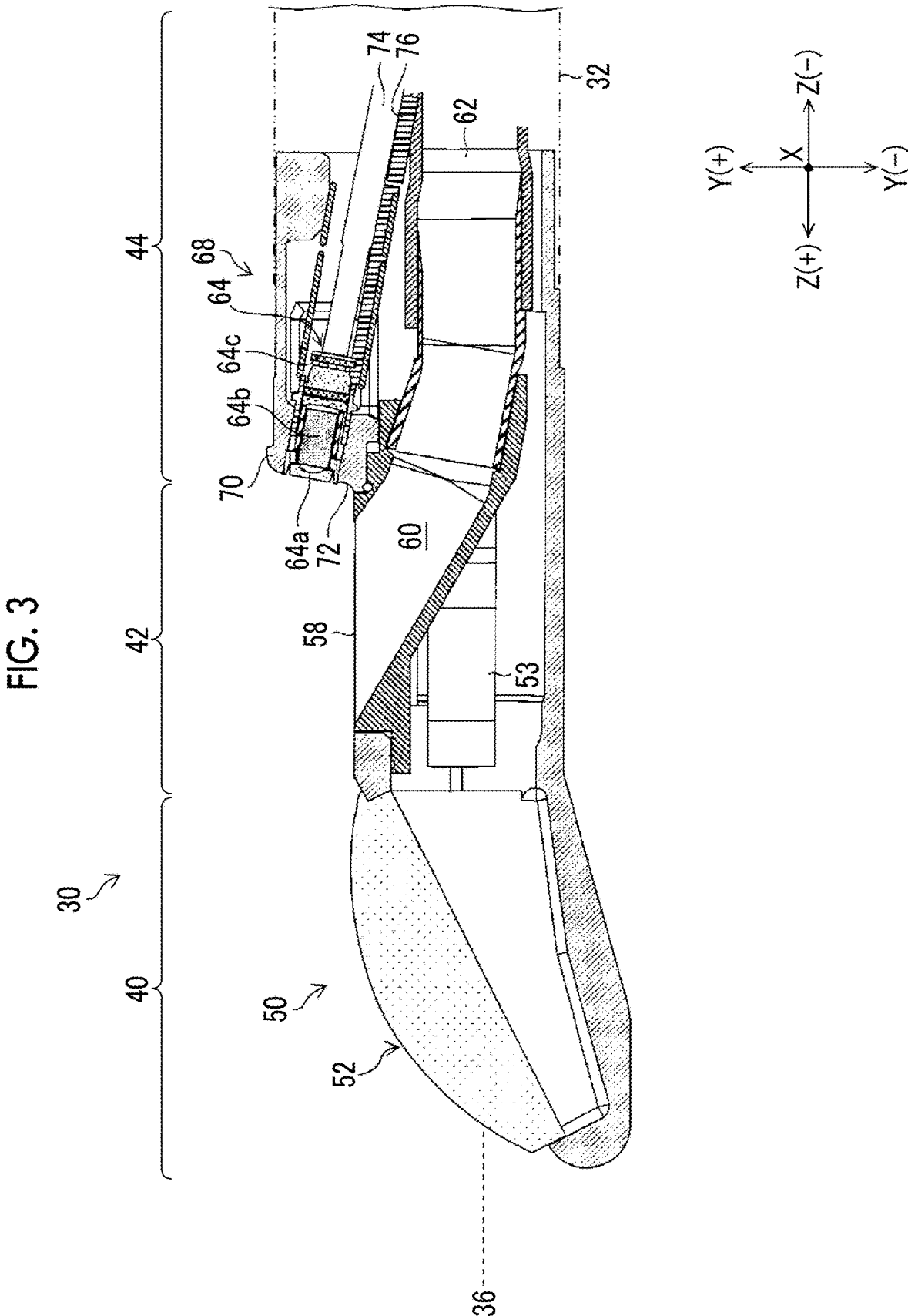
FIG. 3 is a cross-sectional view of the distal end part body.

Next, a configuration of the distal end part body 30 will be described. FIG. 2 is a perspective view of the distal end part body 30. FIG. 3 is a cross-sectional view of the distal end part body 30. In FIG. 2, a puncture needle 90 is shown as an example of the treatment tool led out from a treatment tool outlet port 58 of the distal end part body 30.

In the following description, a three-dimensional orthogonal coordinate system including an X axis, a Y axis, and a Z axis that are orthogonal to each other may be used. A Z direction is a direction parallel to a longitudinal axis 36 of the distal end part body 30 (endoscope insertion part 12). Hereinafter, the Z(+) direction side is also referred to as a distal end side, and the Z(–) direction side opposite to the Z(+) direction side is also referred to as a base end side. In addition, a Y direction is an up-down direction in a case in which the distal end part body 30 is viewed from the distal end side (Z(+) direction side) such that an ultrasonic transducer 50 and the treatment tool outlet port 58 are directed upward. In the following description, the Y(+) direction side is also referred to as an upper side, and the Y(–) direction side is also referred to as a lower side. In addition, an X direction is a left-right direction in a case in which the distal end part body 30 is viewed from the distal end side (Z(+) direction side) such that the ultrasonic transducer 50 and the treatment tool outlet port 58 are directed upward. In the following description, the X(+) direction side is also referred to as a left side, and the X(–) direction side is also referred to as a right side.

As shown in FIGS. 2 and 3, the distal end part body 30 comprises an ultrasonic attachment part 40, an outlet port forming part 42, and a body part 44 from the distal end side to the base end side of the distal end part body 30.

The ultrasonic transducer 50 is attached to the ultrasonic attachment part 40 in a posture of being tilted forward (inclined) to the lower side (Y(–) direction side) with respect to the longitudinal axis 36 in a case in which the distal end part body 30 is viewed from the left-right direction (X direction side). The ultrasonic transducer 50 is of a convex type that has a transducer surface 52 on which a plurality of ultrasonic transducers that transmit and receive ultrasonic waves are arranged in an arc shape along a direction of the longitudinal axis 36. The ultrasound waves are transmitted from each ultrasonic transducer toward a living body, and an ultrasound echo reflected by a living body tissue is received by each ultrasonic transducer. A signal of the ultrasound echo received by each ultrasonic transducer is transmitted to the ultrasound processor device via a signal cable 53.

The ultrasonic attachment part 40 is provided with a pair of standing wall parts 54 mainly formed of surfaces perpendicular to (including a case of being substantially perpendicular to, the same applies hereinafter) the X direction. The pair of standing wall parts 54 are spaced from each other in a width direction (X direction) of the distal end part body 30 (ultrasonic attachment part 40) to face each other, and the ultrasonic transducer 50 is disposed therebetween. That is, in a case in which the distal end part body 30 is viewed from the distal end side (Z(+) direction side), the standing wall part 54 is provided on each side of the ultrasonic transducer 50. In a case in which the distal end part body 30 is viewed from the upper side (Y(+) direction side), a spacing between the pair of standing wall parts 54 (distance in the X direction) is formed shorter than a width (distance in the X direction) of the other portions (outlet port forming part 42 and the body part 44) of the distal end part body 30.

The outlet port forming part 42 is provided with an opening forming surface 56 facing the upper side (Y(+) direction side) as with the ultrasonic transducer 50. The opening forming surface 56 is formed of a surface perpendicular to the Y direction, and has a substantially rectangular shape in plan view. The opening forming surface 56 constitutes a part of an outer peripheral surface (outer surface) of the distal end part body 30.

The treatment tool outlet port 58 that is open upward (toward the Y(+) direction side) is provided on the opening forming surface 56. The treatment tool outlet port 58 is a portion where a distal end side of the treatment tool (in FIG. 2, the puncture needle 90 is shown) inserted from the treatment tool inlet port 22 is led out to the outside. In the present embodiment, although the treatment tool outlet port 58 is open in the planar opening forming surface 56, the treatment tool outlet port 58 may be open in surfaces of various shapes such as a curved surface, an inclined surface, or an uneven surface.

A pipe line 60 is formed inside the outlet port forming part 42 and the body part 44. A distal end side of the pipe line 60 is connected to the treatment tool outlet port 58, and a base end side of the pipe line 60 is connected to the treatment tool insertion channel 62 inserted into the endoscope insertion part 12. As a result, a distal end of the treatment tool (puncture needle 90) inserted from the treatment tool inlet port 22 is guided to the treatment tool outlet port 58 by way of the treatment tool insertion channel 62 and the pipe line 60, and is led out from the treatment tool outlet port 58 to the outside.

The body part 44 comprises an optical system housing part 68 in which an observation optical system 64 and illumination optical systems 66 are disposed. The optical system housing part 68 has a substantially semi-cylindrical shape, and has a convex surface 70 and a stepped surface 72. The convex surface 70 constitutes a part of the outer peripheral surface of the distal end part body 30 (optical system housing part 68). The convex surface 70 is located on the upper side (Y(+) direction side) with respect to the opening forming surface 56, and is formed of a curved surface (a part of a cylindrical shape) having a predetermined length in the direction of the longitudinal axis 36 (Z direction). The convex surface 70 may be formed in various shapes such as a curved surface, an inclined surface, or an uneven surface.

The stepped surface 72 is an inclined surface that connects a base end side of the opening forming surface 56 and a distal end side of the convex surface 70, and constitutes a part of the outer peripheral surface of the distal end part body 30. The inclined surface referred to here also includes a vertical surface having an inclined angle of 90° with respect to the direction of the longitudinal axis 36 (Z direction).

The stepped surface 72 is provided with an observation window 64a of the observation optical system 64 and illumination windows 66a of a pair of the illumination optical systems 66.

The observation optical system 64 includes the observation window 64a provided in the stepped surface 72, and a lens system 64b and an imaging element 64c provided in the optical system housing part 68. The imaging element 64c is a charge coupled device (CCD) type or complementary metal oxide semiconductor (CMOS) type image sensor, and captures an observation image taken in from the observation window 64a via the lens system 64b. Then, the imaging element 64c outputs an imaging signal of the observation image to system constituent devices via a signal cable 74 inserted into the endoscope insertion part 12.

The illumination optical system 66 is provided on both sides of the observation optical system 64 in the left-right direction (X direction) in a case in which the distal end part body 30 is viewed from the distal end side, and includes the illumination window 66a provided on the stepped surface 72 and a light guide 76 inserted into the endoscope insertion part 12. An emission end of the light guide 76 is disposed rearward of each illumination window 66a. As a result, illumination light supplied from the light source device to each light guide 76 is emitted from each illumination window 66a.

As described above, in the distal end part body 30, the ultrasonic transducer 50, the treatment tool outlet port 58, and the stepped surface 72 (observation window 64a) are disposed in order from the distal end side to the base end side. That is, the treatment tool outlet port 58 is disposed between the ultrasonic transducer 50 and the observation window 64a. Therefore, a puncture site by the puncture needle 90 can be observed by the observation optical system 64.

Balloon Unit

Figure 4:
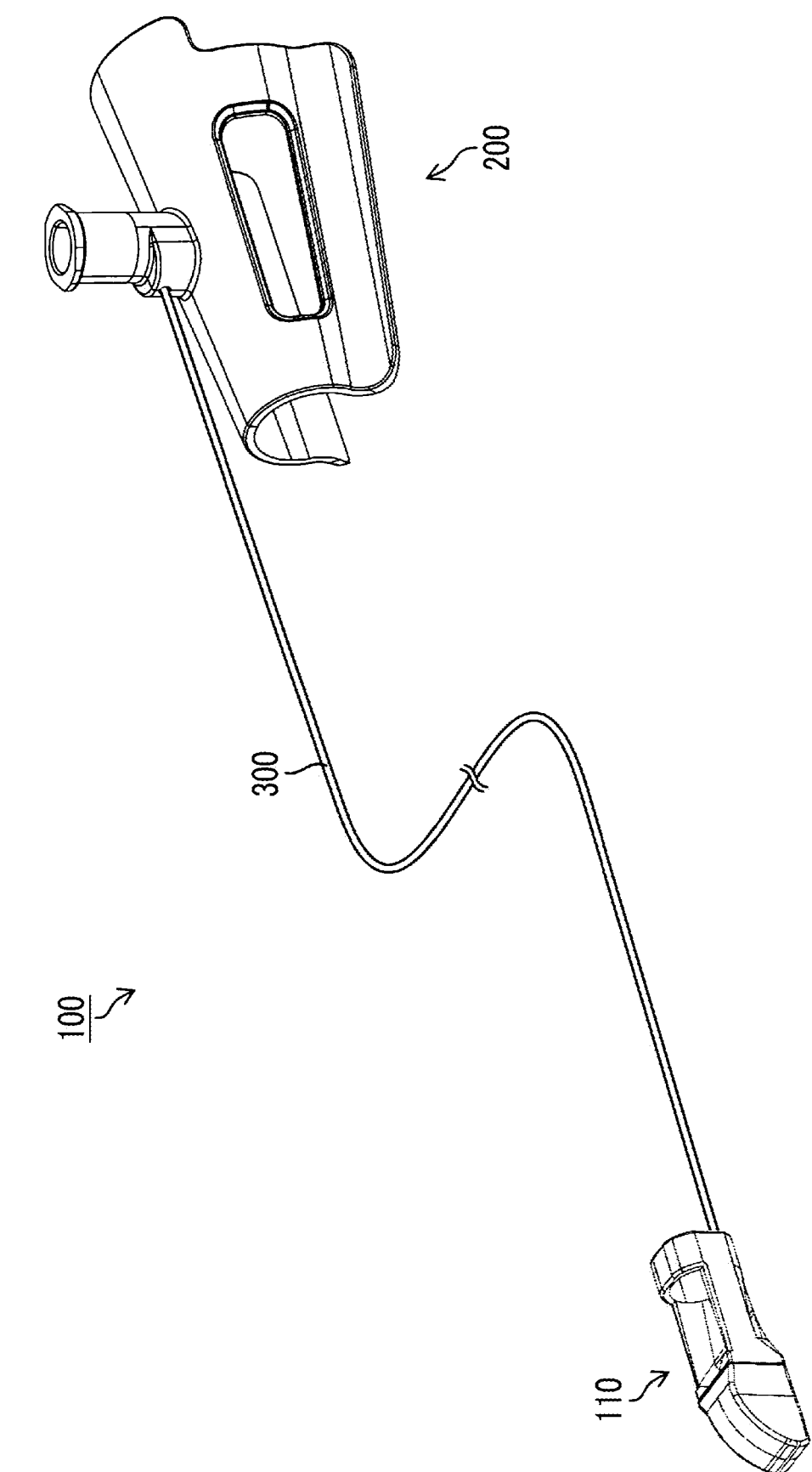
FIG. 4 is a schematic diagram showing a configuration of a balloon unit.

FIG. 4 is a schematic diagram showing a configuration of an endoscope balloon unit 100 (hereinafter, referred to as a "balloon unit 100"). The balloon unit 100 is of an external type that can be attached to and detached from the endoscope 10. As shown in FIG. 4, the balloon unit 100 comprises an endoscope balloon 110 (hereinafter, referred to as a "balloon 110"), an attachment member 200, and a tube 300. The tube 300 is a pipe line member that sends an ultrasonic transmission medium between the balloon 110 and the attachment member 200.

In a case in which the balloon unit 100 is attached to the endoscope 10, the balloon 110 is mounted on the distal end part body 30, and the attachment member 200 is mounted on the operation part 14. The tube 300 is attached to an outer surface of the endoscope insertion part 12 along a longitudinal direction (the direction along the longitudinal axis 36) of the endoscope insertion part 12, for example, using a medical tape. As a method of fixing the tube 300 to the endoscope insertion part 12, a method using a mounting band, an adhesion wrap, a suture thread, or the like may be used in addition to the medical tape.

Balloon

Next, a configuration of the balloon 110 will be described. In the following description, as in the distal end part body 30 described above, a three-dimensional orthogonal coordinate system including an X axis, a Y axis, and a Z axis that are orthogonal to each other may be used. In a case in which the balloon 110 is mounted on the distal end part body 30, the X axis, the Y axis, and the Z axis of the balloon 110 match the X axis, the Y axis, and the Z axis of the distal end part body 30, respectively. A Z direction is a direction parallel to a longitudinal axis 112 of the balloon 110. Hereinafter, the Z(+) direction side is also referred to as a distal end side, and the Z(−) direction side opposite to the Z(+) direction side is also referred to as a base end side. In addition, a Y direction is an up-down direction in a case in which the balloon 110 is viewed from the distal end side (Z(+) direction side) such that an open window 166 of the balloon 110 is directed upward. In the following description, the Y(+) direction side is also referred to as an upper side, and the Y(−) direction side is also referred to as a lower side. In addition, an X direction is a left-right direction in a case in which the balloon 110 is viewed from the distal end side (Z(+) direction side) such that an open window 166 of the balloon 110 is directed upward. In the following description, the X(+) direction side is also referred to as a left side, and the X(−) direction side is also referred to as a right side.

Figure 5:
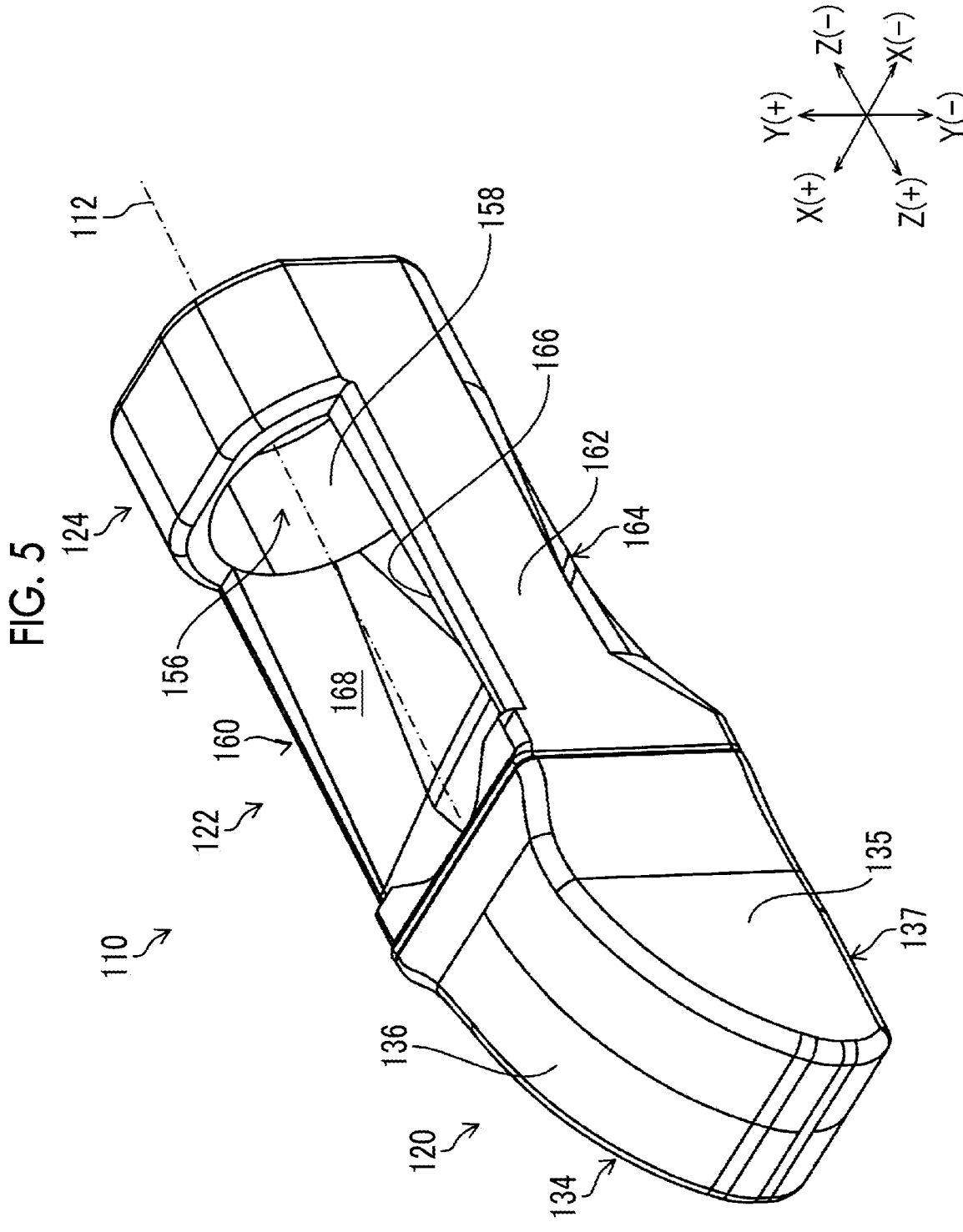
FIG. 5 is a perspective view of a balloon.
Figure 6:
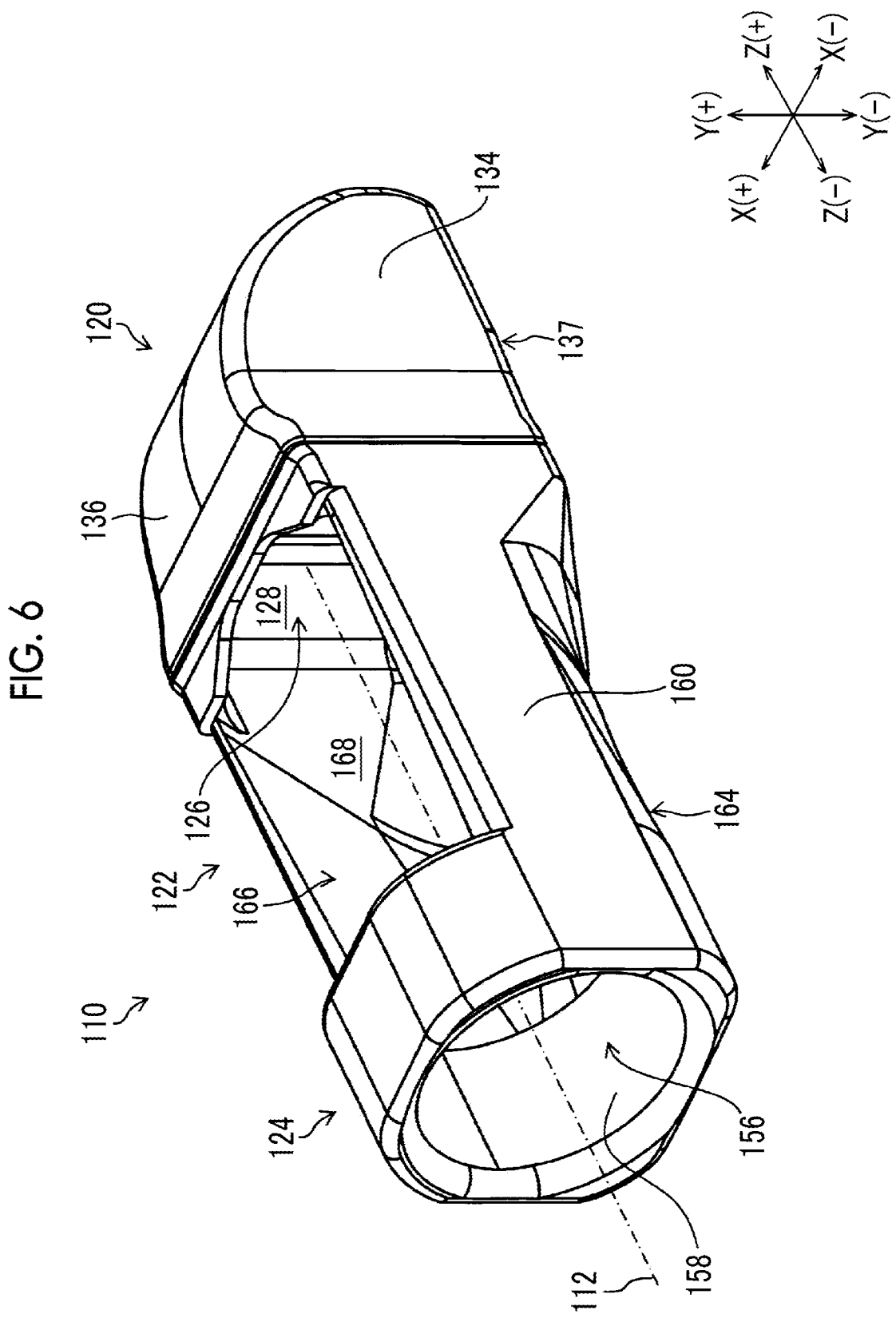
FIG. 6 is a perspective view of the balloon in a case in which the balloon is viewed from an angle different from an angle in FIG. 5.
Figure 7:
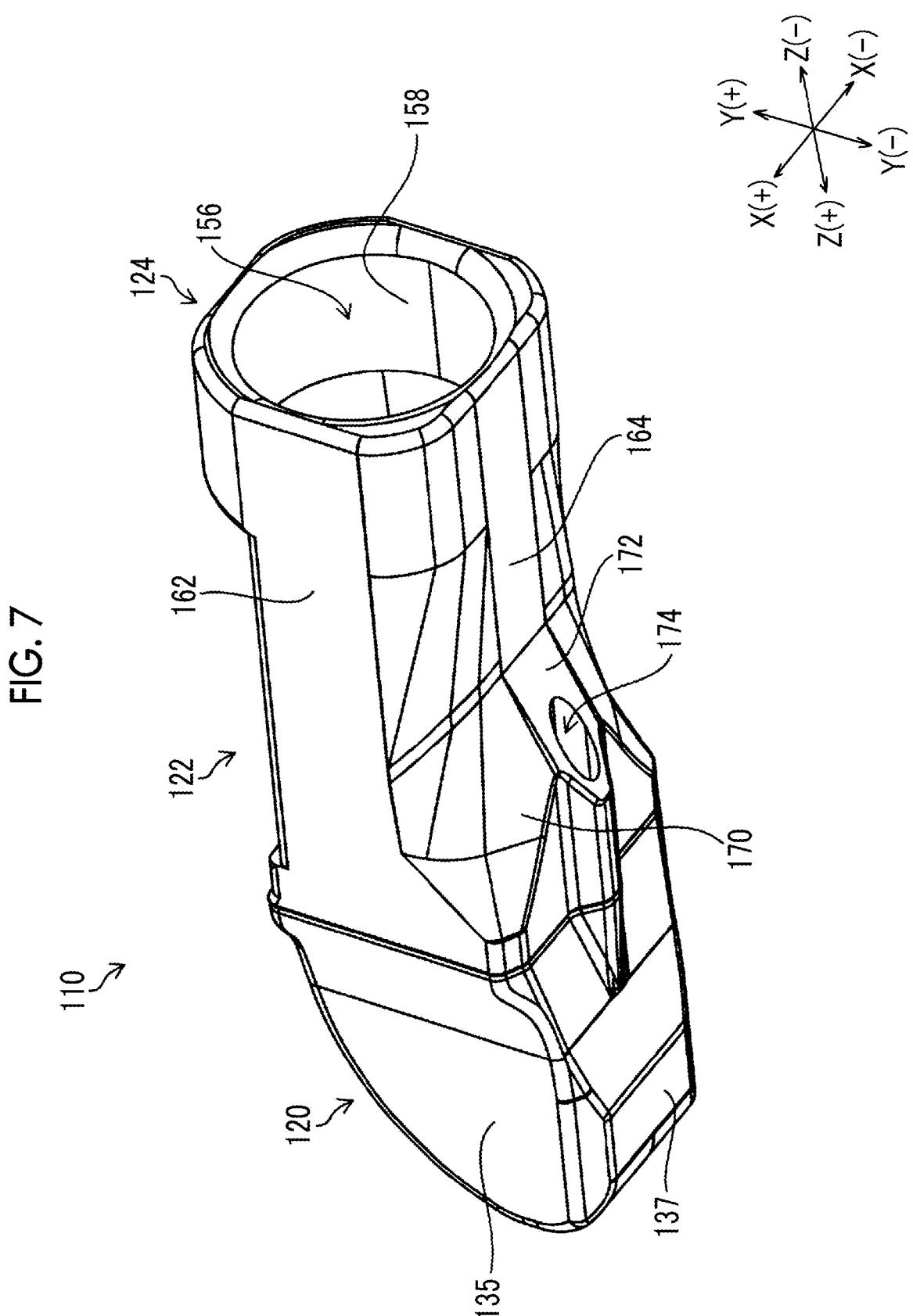
FIG. 7 is a perspective view of the balloon in a case in which the balloon is viewed from an angle different from the angles in FIG. 5 and FIG. 6.
Figure 8:
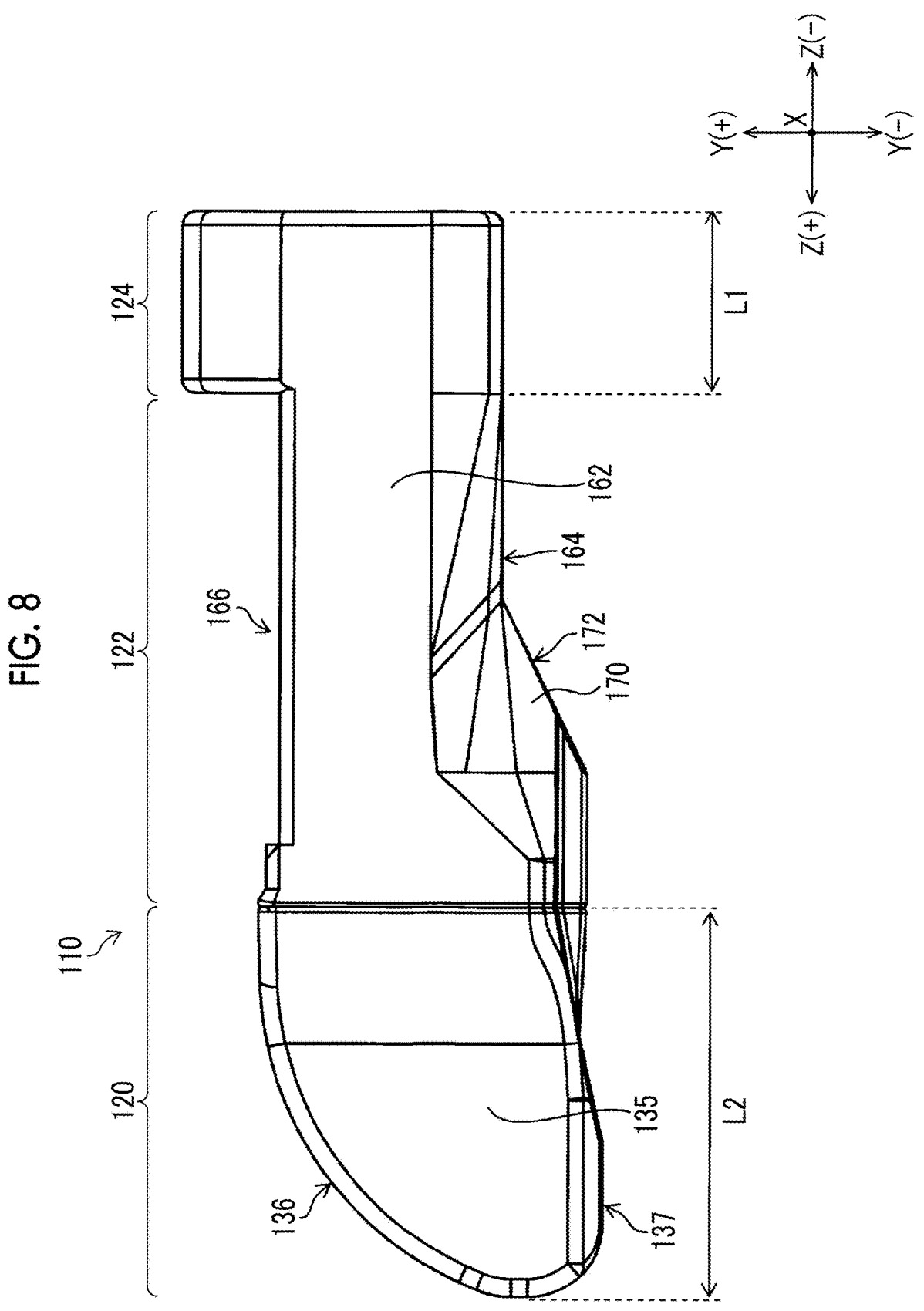
FIG. 8 is a side view of the balloon.

FIG. 5 is a perspective view of the balloon 110. FIG. 6 is a perspective view of the balloon 110 in a case in which the balloon 110 is viewed from an angle different from an angle in FIG. 5. FIG. 7 is a perspective view of the balloon 110 in a case in which the balloon 110 is viewed from an angle different from the angles in FIG. 5 and FIG. 6. FIG. 8 is a side view of the balloon 110.

As shown in FIGS. 5 to 8, the balloon 110 covers the ultrasonic transducer 50 provided in the distal end part body 30 of the endoscope insertion part 12. The balloon 110 has an overall shape based on a tubular shape that matches the shape of the distal end part body 30, and is formed to extend in a direction of the longitudinal axis 112 (Z direction). The balloon 110 comprises a cover body 120, a connecting body 122, and a fixing body 124 in this order from the distal end side to the base end side of the balloon 110.

Cover Body

The cover body 120 is a portion disposed on the distal end side (Z(+) direction side) of the balloon 110. The cover body 120 has a bottomed tubular shape which is closed on the distal end side (Z(+) direction side) in the Z direction (corresponding to a first direction) corresponding to the longitudinal direction (direction of the longitudinal axis 36) of the endoscope insertion part 12 and has an opening portion 126 (see FIG. 6) formed on the base end side (Z(−) direction side). A cover body space portion 128 for accommodating the ultrasonic attachment part 40 is provided inside the cover body 120. The cover body space portion 128 has substantially the same shape (similar shape) as the ultrasonic attachment part 40 and communicates with the opening portion 126. The cover body space portion 128 constitutes a part of a space portion for accommodating the distal end part body 30 inside the balloon 110.

Here, a configuration of the cover body 120 will be described in detail.

Figure 9:
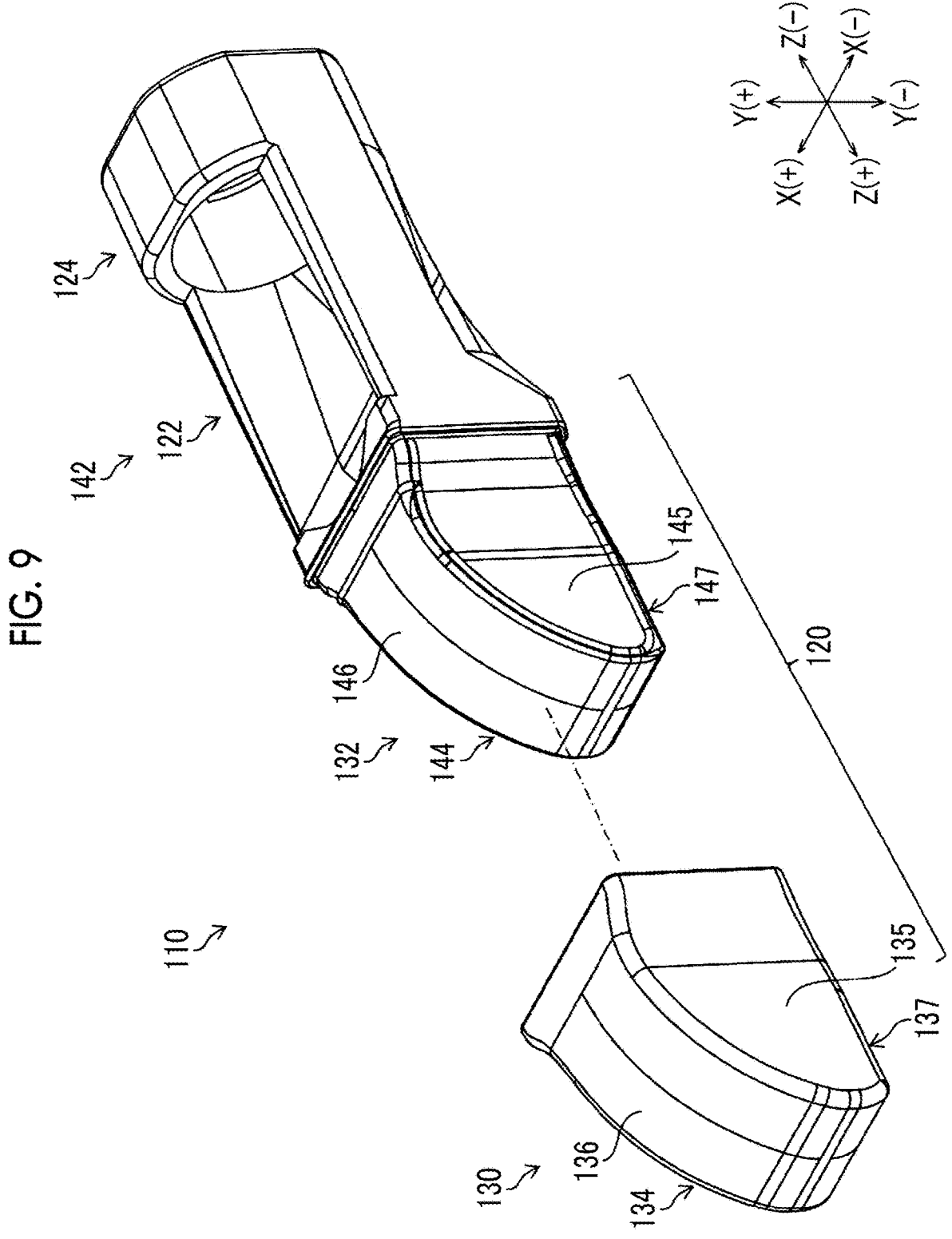
FIG. 9 is an exploded perspective view of the balloon.
Figure 10:
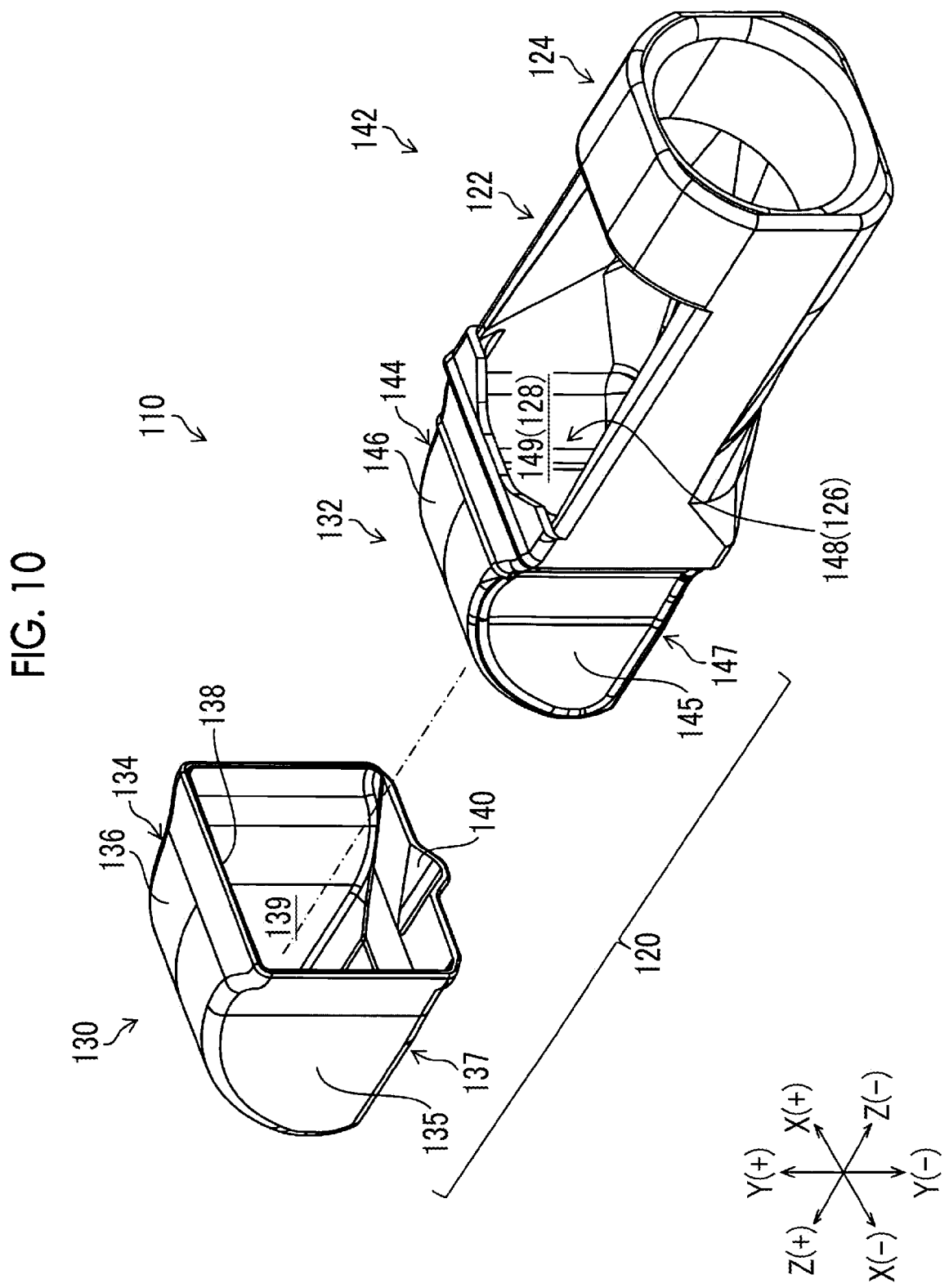
FIG. 10 is an exploded perspective view of the balloon in a case in which the balloon is viewed from an angle different from an angle in FIG. 9.

FIG. 9 is an exploded perspective view of the balloon 110. FIG. 10 is an exploded perspective view of the balloon 110 in a case in which the balloon 110 is viewed from an angle different from an angle in FIG. 9. As shown in FIGS. 9 and 10, the cover body 120 of the balloon 110 is configured as a two-layer structure cover body in which an outer part 130 and an inner part 132 are overlapped.

The outer part 130 is formed of an elastic material such as silicon rubber, and is disposed on an outer side of the cover body 120. The outer part 130 is configured in a bottomed tubular shape by a left side surface portion 134, a right side surface portion 135, an inclined surface portion 136, and a bottom surface portion 137. That is, a distal end side of the outer part 130 is closed by the left side surface portion 134, the right side surface portion 135, the inclined surface portion 136, and the bottom surface portion 137, and an outer opening portion 138 is provided on a base end side of the outer part 130. An outer space portion 139 for accommodating the inner part 132 is provided inside the outer part 130. The outer space portion 139 communicates with the outer opening portion 138.

The left side surface portion 134 and the right side surface portion 135 are disposed on a left side and a right side in the outer part 130, respectively, and are each mainly formed of a surface substantially perpendicular to the X direction. In a case in which the balloon 110 is mounted on the distal end part body 30, the left side surface portion 134 and the right side surface portion 135 are disposed at positions facing the standing wall parts 54 of the distal end part body 30 (ultrasonic attachment part 40), respectively. Base end parts of the left side surface portion 134 and the right side surface portion 135 have a shape in which a spacing between the left side surface portion 134 and the right side portion 135 increases toward the base end side in accordance with shapes of the standing wall parts 54 that the left side surface portion 134 and the right side surface portion 135 face (the same applies to the inner part 132 described below).

The inclined surface portion 136 is disposed on an upper side (Y(+) direction side) of the outer part 130. The inclined surface portion 136 has a shape that follows the shape of the transducer surface 52 of the ultrasonic transducer 50. That is, the inclined surface portion 136 is inclined in a curved shape such that a normal line of the inclined surface portion 136 is directed from the upper side toward the distal end side as the inclined surface portion 136 goes toward the distal end side. The inclined surface portion 136 is disposed at a position facing the transducer surface 52 of the ultrasonic transducer 50 in a case in which the balloon 110 is mounted on the distal end part body 30.

The bottom surface portion 137 is disposed on a lower side (Y(−) direction side) of the outer part 130. The bottom surface portion 137 is connected to the left side surface portion 134 and the right side surface portion 135 on both sides in the left-right direction (X direction), and is connected to the inclined surface portion 136 on the distal end side. A portion of the bottom surface portion 137 on the distal end side is formed of a surface perpendicular to the Y direction, and a portion of the bottom surface portion 137 on the base end side with respect to the portion on the distal end side is formed of an inclined surface having a normal line including components in each of a lower side direction and a base end side direction (see FIGS. 7 and 8). A groove portion 140 constituting a communication path, which will be described below, is provided in a portion of the bottom surface portion 137 on the base end side (see FIG. 10).

The inner part 132 is formed of an elastic material such as silicon rubber, and is disposed inside the outer part 130 in the cover body 120. The inner part 132 is configured as an integrally formed object 142 with the connecting body 122 and the fixing body 124. The inner part 132 is a portion that constitutes a distal end side of the integrally formed object 142.

The inner part 132 has the same shape (similar shape) as the outer part 130. That is, the inner part 132 has a bottomed tubular shape formed by a left side surface portion 144, a right side surface portion 145, an inclined surface portion 146, and a bottom surface portion 147. The inner part 132 and the outer part 130 may have partially different shapes (dissimilar shapes) as long as the shapes are substantially the same.

A distal end side of the inner part 132 is closed by the left side surface portion 144, the right side surface portion 145, the inclined surface portion 146, and the bottom surface portion 147. In addition, an inner opening portion 148 is provided on a base end side of the inner part 132 (see FIG. 10). The inner opening portion 148 corresponds to the opening portion 126 of the cover body 120. An inner space portion 149 defined by the left side surface portion 144, the right side surface portion 145, the inclined surface portion 146, and the bottom surface portion 147 is provided inside the inner part 132. The inner space portion 149 communicates with the inner opening portion 148. The inner space portion 149 corresponds to the cover body space portion 128 of the cover body 120.

Configurations (arrangement and orientation) of the left side surface portion 144, the right side surface portion 145, the inclined surface portion 146, and the bottom surface portion 147 in the inner part 132 are the same as the configurations of the left side surface portion 134, the right side surface portion 135, the inclined surface portion 136, and the bottom surface portion 137 in the outer part 130, and description thereof will be omitted to avoid redundancy in the description.

The left side surface portion 144 and the right side surface portion 145 are portions that constitute a cover body fixing portion that is fixed to the distal end part body 30, and include fixing surfaces facing each other in the X direction (corresponding to a second direction). The left side surface portion 144 and the right side surface portion 145 elastically hold the distal end part body 30 with the fixing surfaces.

In a state before the balloon 110 is mounted on the distal end part body 30, a spacing (distance in the X direction) between the left side surface portion 144 and the right side surface portion 145 of the inner part 132 is set smaller than the spacing (distance in the X direction) between the pair of standing wall parts 54 by about 10% to 20%. As a result, in a case in which the balloon 110 is mounted on the distal end part body 30 and the ultrasonic attachment part 40 is accommodated in the inner space portion 149 (cover body space portion 128), the left side surface portion 144 and the right side surface portion 145 are fixed in a state of being in close contact with the corresponding standing wall parts 54, respectively, by an elastic force (contractile force) that acts in a direction in which the left side surface portion 144 and the right side surface portion 145 approach each other.

The outer part 130 is overlapped on an outer side of the inner part 132 configured in this way, thereby forming the cover body 120. Specifically, as shown in FIGS. 9 and 10, the inner part 132 is accommodated in the outer space portion 139 via the outer opening portion 138 of the outer part 130 in a state in which relative positions of the outer part 130 and the inner part 132 are aligned such that the left side surface portion 134, the right side surface portion 135, the inclined surface portion 136, and the bottom surface portion 137 in the outer part 130 face the left side surface portion 144, the right side surface portion 145, the inclined surface portion 146, and the bottom surface portion 147 in the inner part 132. In this case, the outer part 130 and the inner part 132 are integrated by being bonded together on the base end side (Z(−) direction side) which is an opening side of each of the outer part 130 and the inner part 132. As a result, the cover body 120 having a two-layer structure in which the outer part 130 and the inner part 132 are overlapped is configured.

Figure 11:
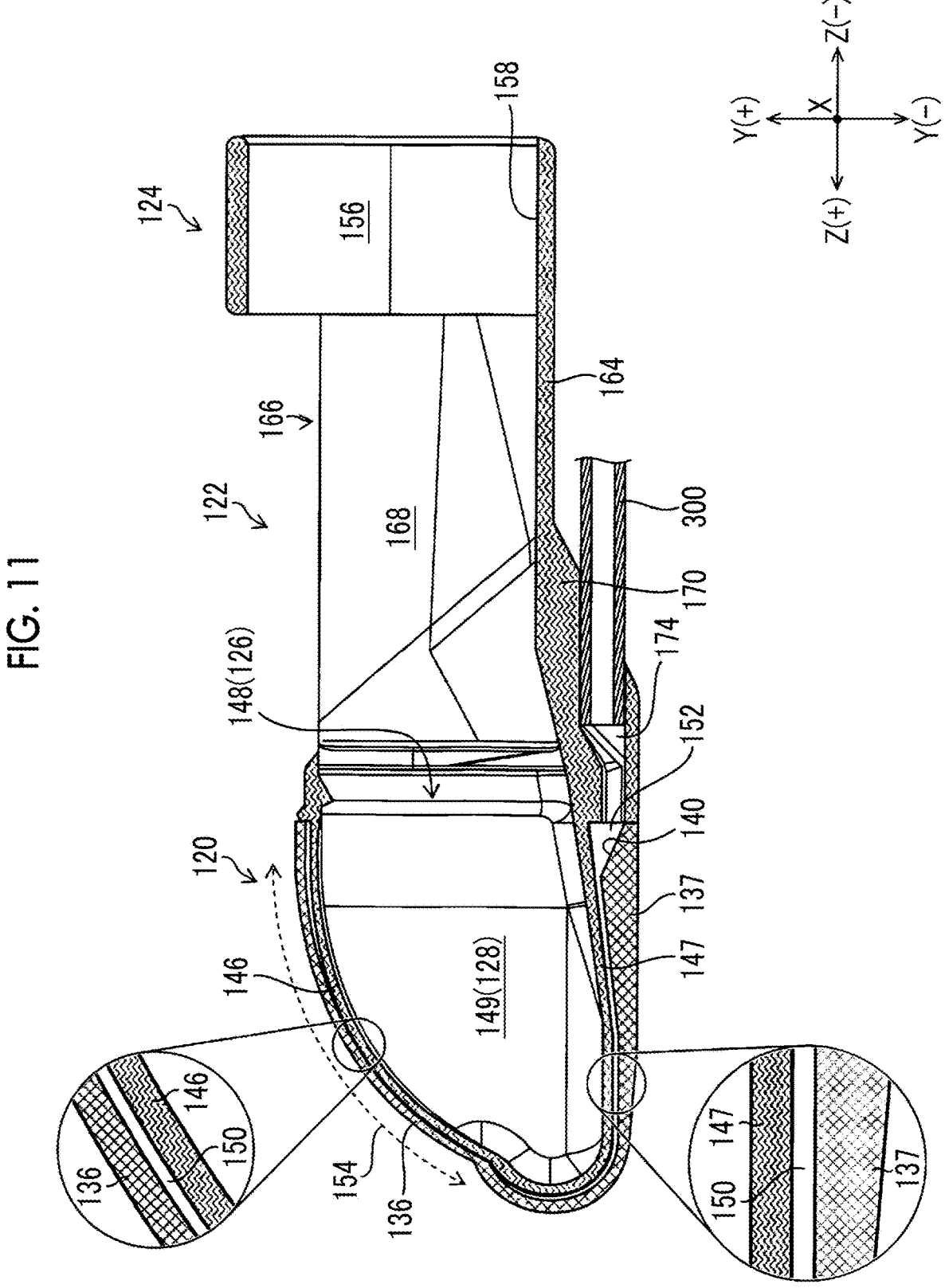
FIG. 11 is a side cross-sectional view of a cover body.

FIG. 11 is a side cross-sectional view of the cover body 120. As shown in FIG. 11, in the cover body 120, the outer part 130 and the inner part 132 are bonded together on the opening side (base end side), so that an inner space (sealed space) is formed in a gap between the outer part 130 and the inner part 132. The internal space is a storage part 150 in which the ultrasonic transmission medium is stored.

The storage part 150 is provided in a gap between the outer part 130 and the inner part 132. Specifically, the storage part 150 is formed of gap spaces between the inclined surface portion 136 and the bottom surface portion 137 in the outer part 130 and the corresponding inclined surface portion 146 and the corresponding bottom surface portion 147 in the inner part 132, and the spaces communicate with each other on the distal end side. The left side surface portion 134 and the right side surface portion 135 in the outer part 130 are fully adhered to the corresponding left side surface portion 144 and the corresponding right side surface portion 145 in the inner part 132, and a gap is not provided therebetween.

The cover body 120 is provided with a communication path 152 between the groove portion 140 (see FIG. 10) provided in the bottom surface portion 137 of the outer part 130 and the bottom surface portion 147 of the inner part 132. One end of the communication path 152 communicates with the storage part 150. In addition, the other end of the communication path 152 communicates with a tube connection port 174, which will be described below.

Of the inclined surface portion 136 of the outer part 130, at least a region facing the transducer surface 52 of the ultrasonic transducer 50 is a bulging portion 154 that is more likely to bulge outward than other regions (including the left side surface portion 134, the right side surface portion 135, and the bottom surface portion 137). The bulging portion 154 is configured as a region having a smaller thickness than other regions. The bulging portion 154 may be provided only in a region of the inclined surface portion 136 of the outer part 130 that faces the transducer surface 52 of the ultrasonic transducer 50, or may be provided over the entire inclined surface portion 136.

In addition, in order to suppress bulging of portions other than the bulging portion 154, for example, a bulge restricting portion (thick portion or adhesion portion) disclosed in JP2023-47488A may be provided around the bulging portion 154. The bulge restricting portion suppresses bulging of portions other than the bulging portion 154 in a case in which the ultrasonic transmission medium is supplied to the storage part 150. A specific configuration of the bulge restricting portion is known, and thus description thereof will be omitted here.

Figure 12:
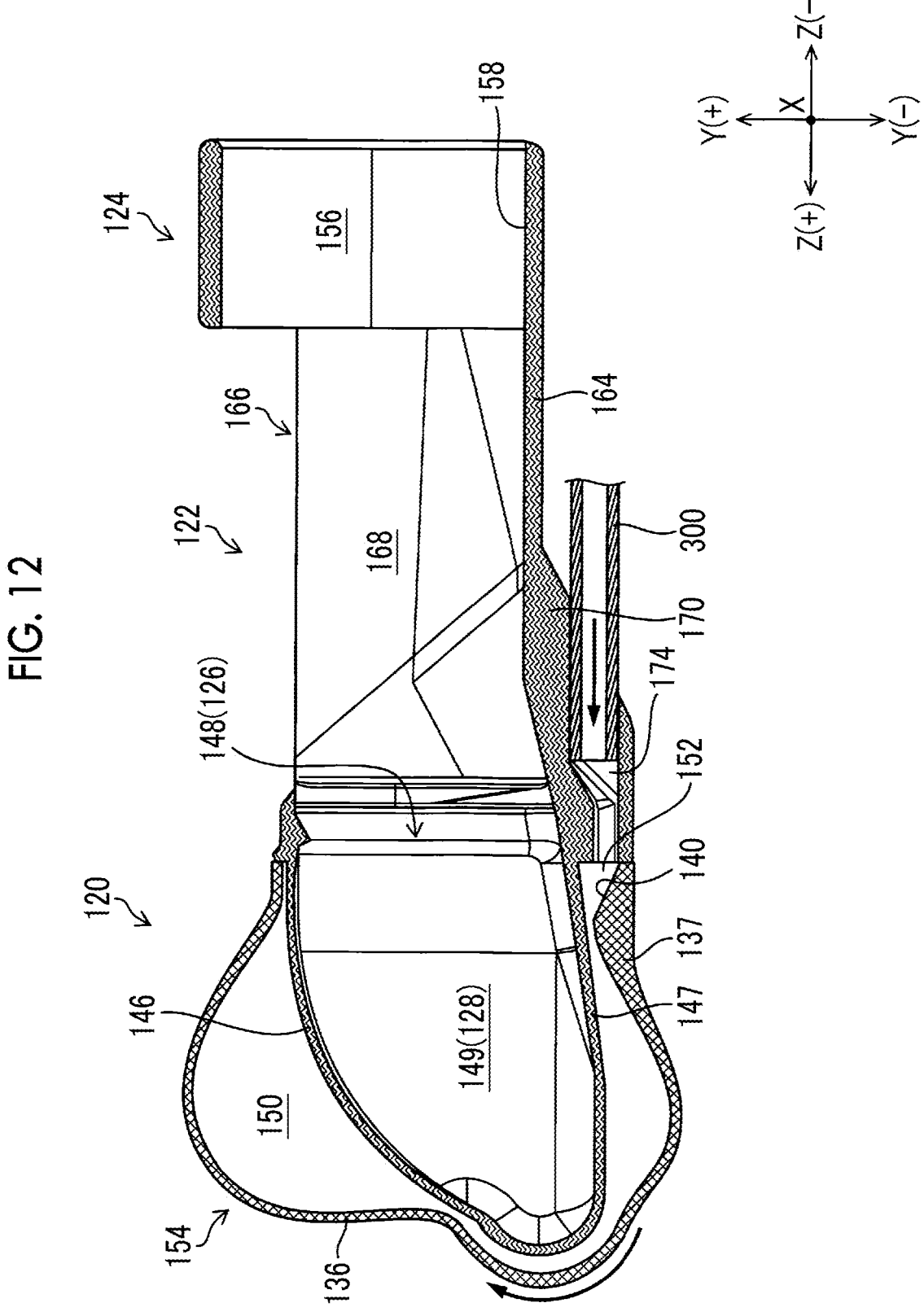
FIG. 12 is a diagram showing a state in which a bulging portion of an outer part bulges outward in a case in which an ultrasonic transmission medium is supplied to a storage part.

FIG. 12 is a diagram showing a state in which the bulging portion 154 of the outer part 130 bulges outward in a case in which the ultrasonic transmission medium is supplied to the storage part 150. As shown in FIG. 12, in a case in which the ultrasonic transmission medium is supplied to the storage part 150 from the tube 300 connected to the tube connection port 174 via the communication path 152, as shown by a bold line arrow in FIG. 12, the ultrasonic transmission medium passes through the storage part 150 on the lower side (bottom surface portion 147 side) of the inner part 132, the ultrasonic transmission medium is collected in the storage part 150 on the upper side (inclined surface portion 146 side) of the inner part 132 (that is, the storage part 150 at a position where the bulging portion 154 of the outer part 130 is provided), and the bulging portion 154 bulges outward. In a case in which the ultrasonic transmission medium is supplied to the storage part 150, as shown in FIG. 12, the bottom surface portion 137 of the outer part 130 also bulges outward, but the bulging amount thereof is smaller than the bulging amount of the bulging portion 154 of the outer part 130.

With the cover body 120 configured as described above, the storage part 150 in which the ultrasonic transmission medium is stored is provided in the gap between the outer part 130 and the inner part 132, and the bulging portion 154 is provided in the outer part 130. The bulging portion 154 is provided in a region facing the transducer surface 52 of the ultrasonic transducer 50, and is a portion that is more likely to bulge than other regions. As a result, by means of the ultrasonic transmission medium stored in the storage part 150, the bulging portion 154 bulges outward more than regions of the outer part 130 other than the bulging portion 154 while the bulging of the other regions is suppressed. Therefore, it is possible to insert the distal end part body 30 on which the balloon 110 is mounted into a narrow lumen of a bronchus.

In addition, in the cover body 120, since the gap between the outer part 130 and the inner part 132 serves as the storage part 150, it is preferable that a predetermined clearance is provided between the outer part 130 and the inner part 132. In addition, the outer part 130 and the inner part 132 may be made of different materials so that the outer part 130 and the inner part 132 do not stick to each other. In any case, the outer part 130 and the inner part 132 can be prevented from sticking to each other.

Fixing Body

Next, a configuration of the fixing body 124 will be described.

As shown in FIGS. 5 to 8, the fixing body 124 is a portion disposed on the base end side (Z(−) direction side) of the balloon 110. The fixing body 124 is formed of a tubular body having a through-passage 156 that penetrates in the Z direction. The through-passage 156 has a size (inner diameter) that allows the distal end part body 30 to be inserted therethrough, and the opening portion 126 of the cover body 120 is provided at a position intersecting an extension direction of an axis of the through-passage 156. The through-passage 156 constitutes a part of a space portion for accommodating the distal end part body 30 inside the balloon 110. A fixing surface 158 (inner peripheral surface of the through-passage 156) that is fixed to a base end part of the distal end part body 30 (at least on the base end side with respect to the stepped surface 72 of the outlet port forming part 42) is provided inside the fixing body 124. The base end part of the distal end part body 30 is an example of a "fixed part" according to the present invention.

The fixing body 124 constitutes a part of the integrally formed object 142 described above, and is integrally formed with the inner part 132 and the connecting body 122. The fixing body 124 is formed of an elastic material such as silicon rubber, similarly to the inner part 132.

An inner diameter (inner diameter of the through-passage 156) of the fixing body 124 is formed smaller than an outer diameter of the base end part of the distal end part body 30 by about 10% (percent, the same applies hereinafter) to 20%. Therefore, in a case in which the distal end part body 30 is inserted into the through-passage 156 of the fixing body 124 and the fixing body 124 is fixed to the base end part of the distal end part body 30, the fixing body 124 is closely fixed to the base end part of the distal end part body 30 by an elastic force in a diameter-reduced direction of the fixing body 124.

In the present specification, the term "closely fixed" means that the members are fixed in a state of being in close contact with each other without a gap therebetween. As long as the fixing body 124 is fixed to the base end part of the distal end part body 30, the fixing body 124 does not need to be necessarily closely fixed. For example, a gap may be formed in a portion between the fixing surface 158 of the fixing body 124 and the base end part of the distal end part body 30. Note that from the viewpoint of reliably fixing the balloon 110 to the distal end part body 30, it is preferable that the fixing body 124 is closely fixed over the entire circumference of the base end part of the distal end part body 30.

As shown in FIG. 8, a length (length in the Z direction) L1 of the fixing body 124 is preferably in a range of 30% or more and 90% or less with respect to a length (length in the Z direction) L2 of the cover body 120. In the present example, the length L1 of the fixing body 124 is about 50% with respect to the length L2 of the cover body 120. Since the fixing body 124 has a length in the above-described range, an area in which the fixing body 124 is fixed (preferably, closely fixed) to the base end part of the distal end part body 30 is increased, thereby improving the fixation of the balloon 110 to the distal end part body 30.

A position (position in the Z direction) of the fixing body 124 in the balloon 110 is preferably set in a range of 20 mm (millimeters, the same applies hereinafter) or more and 60 mm or less from a distal end of the balloon 110 (cover body 120). By increasing a distance (distance in the Z direction) between the fixing body 124 and the cover body 120, a fixing force of the balloon 110 to the distal end part body 30 can be increased. However, in a case in which the distance between the fixing body 124 and the cover body 120 is too long, the attachment and detachment of the balloon 110 with respect to the distal end part body 30 takes time and effort. Therefore, it is preferable that the position of the fixing body 124 in the balloon 110 is set in the above-described range. In the present embodiment, the base end part of the distal end part body 30 is shown as an example of the fixed part of the endoscope insertion part 12 to which the fixing body 124 is fixed, but the present disclosure is not limited to this, and the fixed part may be the bendable part 32 (preferably, a distal end part of the bendable part 32).

Connecting Body

Next, a configuration of the connecting body 122 will be described.

As shown in FIGS. 5 to 8, the connecting body 122 is a portion disposed between the cover body 120 and the fixing body 124 in the balloon 110. The connecting body 122 connects the cover body 120 (inner part 132) and the fixing body 124 to each other.

The connecting body 122 constitutes a part of the integrally formed object 142 described above, and is integrally formed with the inner part 132 and the fixing body 124. The connecting body 122 is formed of an elastic material such as silicon rubber, similarly to the inner part 132.

The connecting body 122 has a gutter shape that is open on the upper side (Y(+) direction side), and is provided to extend in the direction of the longitudinal axis 112 (Z direction). The connecting body 122 is configured such that a cross section (XY cross section) perpendicular to the longitudinal axis 112 is U-shaped.

The connecting body 122 is formed of a left side surface portion 160, a right side surface portion 162, and a bottom surface portion 164, and is provided with an open window 166 on the upper side. A connecting body space portion 168 defined by the left side surface portion 160, the right side surface portion 162, and the bottom surface portion 164 is provided inside the connecting body 122. The connecting body space portion 168 communicates with the open window 166. In addition, the connecting body space portion 168 communicates with the cover body space portion 128 on a distal end side via the opening portion 126 and communicates with the through-passage 156 on a base end side.

The connecting body space portion 168 constitutes a part of a space portion for accommodating the distal end part body 30 inside the balloon 110, and serves as a space portion for accommodating the outlet port forming part 42 and the body part 44 of the distal end part body 30. In addition, in a case in which the balloon 110 is mounted on the distal end part body 30, the open window 166 of the connecting body 122 exposes the treatment tool outlet port 58, the observation window 64a, and each illumination window 66a to the outside.

As shown in FIGS. 7 and 8, on a distal end side of the bottom surface portion 164 of the connecting body 122, a thick portion 170 that is thicker than on a base end side is provided. The thick portion 170 is formed to protrude to the lower side (Z(−) direction side) with respect to a portion on the base end side of the connecting body 122, and an inclined surface 172 having a normal line including components in each of the lower side direction and the base end side direction is provided on a base end side of the thick portion 170. The tube connection port 174 is formed on the inclined surface 172. The tube connection port 174 communicates with the storage part 150 of the cover body 120 via the communication path 152. The tube connection port 174 may be provided on the cover body 120 instead of the connecting body 122. The tube connection port 174 is a portion to which the tube 300 is connected (see FIGS. 11 and 12), and is an example of a "communication port" according to the present invention.

In the present embodiment, as a preferred aspect, the configuration has been described in which the connecting body 122 has the left side surface portion 160, the right side surface portion 162, and the bottom surface portion 164 and has a gutter shape with the open window 166 on the upper side, but the present invention is not limited to this, and the connecting body 122 may have a shape other than the gutter shape as long as the connecting body 122 can connect the cover body 120 (inner part 132) and the fixing body 124. For example, the connecting body 122 may comprise any one or two of the left side surface portion 160, the right side surface portion 162, or the bottom surface portion 164. In addition, the left side surface portion 160, the right side surface portion 162, and the bottom surface portion 164 are configured in a planar shape along the outer peripheral surface of the distal end part body 30, but the present invention is not limited to this, and may be configured in a strip shape or a rod shape, for example. In addition, a slit or a small hole may be provided in a part of the left side surface portion 160, the right side surface portion 162, and the bottom surface portion 164.

Method of Mounting Balloon

Figure 13:
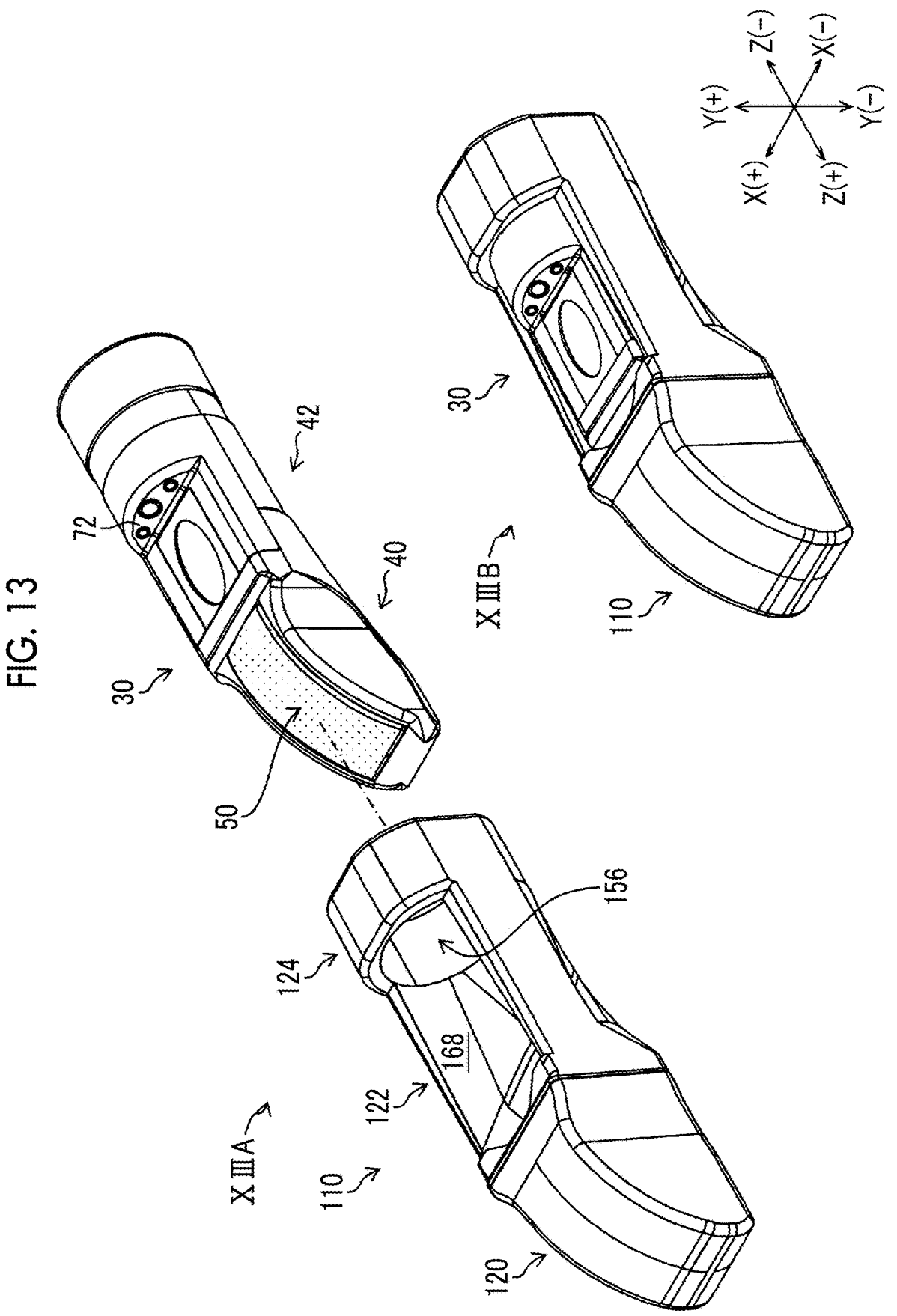
FIG. 13 is a diagram for describing a method of mounting the balloon on the distal end part body.

FIG. 13 is a diagram for describing a method of mounting the balloon 110 on the distal end part body 30. XIIIA of FIG. 13 shows a state before the balloon 110 is mounted on the distal end part body 30, and XIIIB of FIG. 13 shows a state after the balloon 110 is mounted on the distal end part body 30.

In a case in which the balloon 110 is mounted on the distal end part body 30, first, as shown in XIIIA of FIG. 13, the distal end part body 30 and the balloon 110 are arranged in a substantially straight line. In this case, relative positions of the balloon 110 and the distal end part body 30 are aligned such that the base end side (the side on which the fixing body 124 is disposed) of the balloon 110 faces the distal end side (the side on which the ultrasonic transducer 50 is disposed) of the distal end part body 30.

Next, the balloon 110 is pushed straight into the distal end part body 30 such that the distal end part body 30 is inserted into the through-passage 156 of the balloon 110 (fixing body 124). Then, in a case in which the balloon 110 is further pushed until the ultrasonic attachment part 40 of the distal end part body 30 is accommodated in the cover body space portion 128 of the cover body 120, as shown in XIIIB of FIG. 13, the balloon 110 is mounted on the distal end part body 30. In this state, the outlet port forming part 42 of the distal end part body 30 is accommodated in the connecting body space portion 168 of the connecting body 122. In addition, the fixing body 124 of the balloon 110 is fixed to the base end part of the distal end part body 30 (at least on the base end side with respect to the stepped surface 72 of the outlet port forming part 42). In this case, since the fixing body 124 of the balloon 110 is closely fixed to the base end part of the distal end part body 30 by the elastic force in the diameter-reduced direction, it is possible to improve the fixation of the balloon 110 to the distal end part body 30.

In addition, in a state in which the balloon 110 is mounted on the distal end part body 30, the ultrasonic attachment part 40 is elastically held by a pair of side surface portions (the left side surface portion 144 and the right side surface portion 145 of the inner part 132) spaced from each other in the left-right direction (X direction) in the cover body 120 to face each other, in addition to the fixation by the fixing body 124 of the balloon 110, so that the cover body 120 is fixed in a state of being in close contact with the standing wall parts 54 of the ultrasonic attachment part 40.

Effect of Balloon

With the balloon 110 according to the present embodiment configured as described above, the configuration is adopted in which the balloon 110 comprises the cover body 120 having a two-layer structure in which the outer part 130 and the inner part 132 are overlapped, and the fixing body 124 connected to the cover body 120 via the connecting body 122, and the fixing body 124 is fixed to the fixed part (the distal end part body 30 or the bendable part 32) of the endoscope insertion part 12. Therefore, the fixation of the balloon 110 to the distal end part body 30 can be improved.

In addition, since the balloon 110 according to the present embodiment has a configuration in which the balloon 110 is fixed by elastically holding the ultrasonic attachment part 40 by a pair of side surface portions (the left side surface portion 144 and the right side surface portion 145) spaced from each other in the left-right direction (X direction) of the cover body 120 to face each other, in addition to the fixation by the fixing body 124, more stable fixation can be ensured in conjunction with the above-described effect.

In the present embodiment, the aspect in which both the fixation by the fixing body 124 and the fixation by the pair of side surface portions of the cover body 120 are provided has been described, but the present invention is not limited to this, and only the fixing by the fixing body 124 may be provided. In this case, a spacing between the pair of side surface portions of the cover body 120 (the distance in the X direction) is set such that the pair of side surface portions weakly sandwich the ultrasonic attachment part 40 or are in contact with the ultrasonic attachment part 40 to a slight extent.

In addition, in the present embodiment, the configuration has been described in which the cover body 120 has a two-layer structure in which the outer part 130 and the inner part 132 are overlapped, but the present invention is not limited to this, and the cover body 120 may be formed of three or more layers as long as the storage part 150 that stores the ultrasonic transmission medium can be provided inside the cover body 120. In addition, in the present embodiment, the entire cover body 120 is formed of a two-layer structure, but the present invention is not limited to this, and only a part of the cover body 120 may be formed of two layers (or three or more layers).

Attachment Member

Next, a configuration of the attachment member 200 will be described. In the following description, an attachment member according to a first configuration example is denoted by reference numeral 200A, and an attachment member according to a second configuration example is denoted by reference numeral 200B. In addition, in a case in which these attachment members 200A and 200B are collectively referred to, the attachment members 200A and 200B are referred to as an attachment member 200.

First Configuration Example

Figure 14:
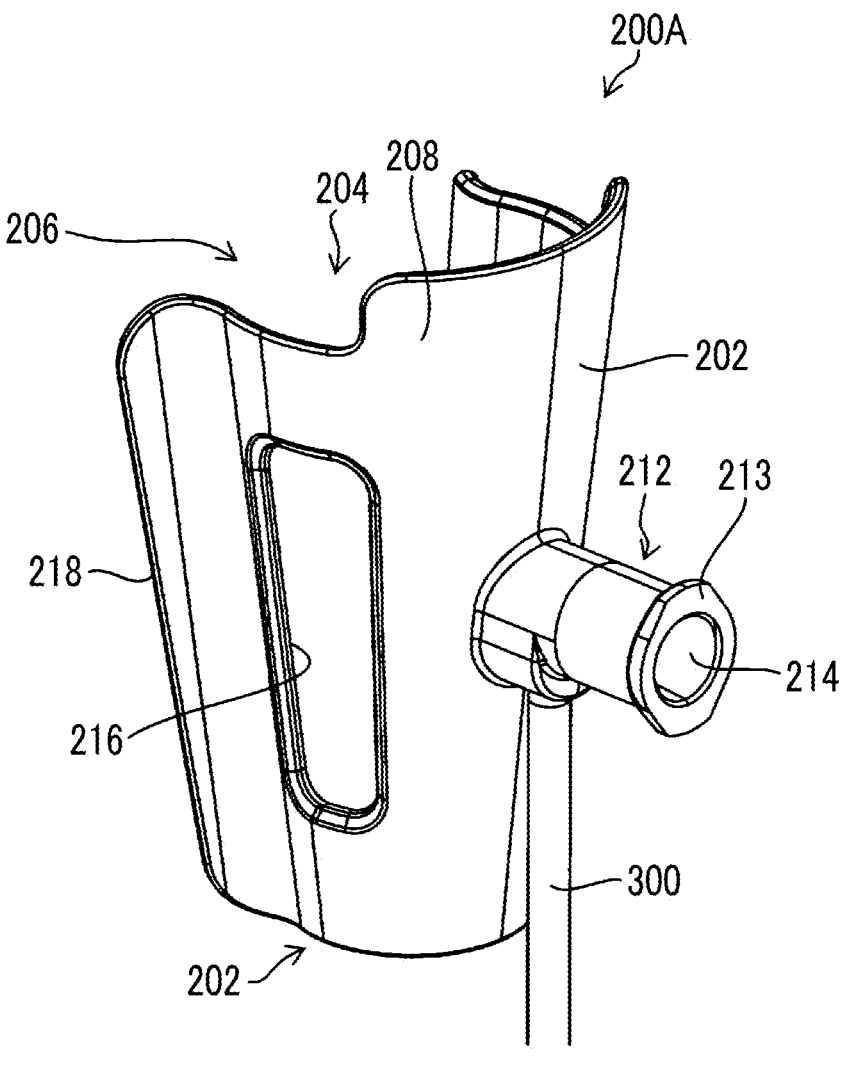
FIG. 14 is a perspective view of an attachment member according to a first configuration example.
Figure 15:
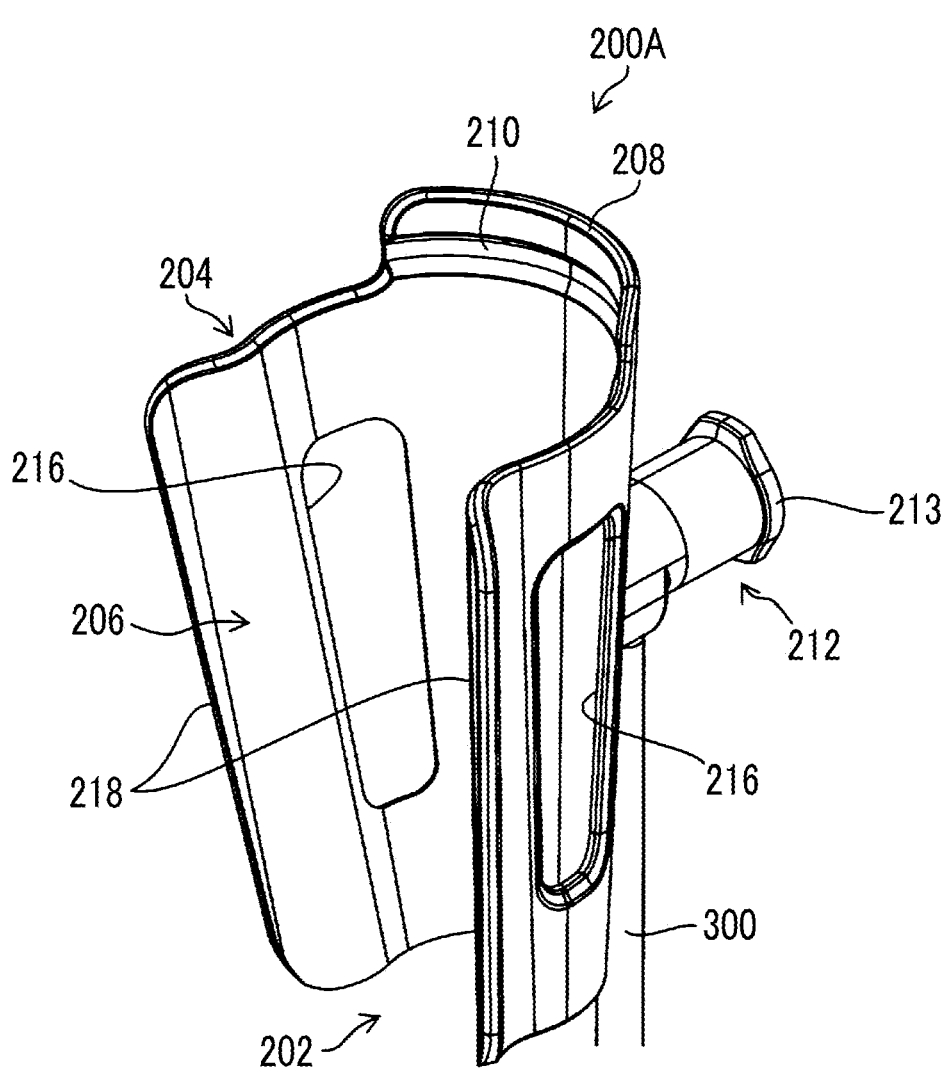
FIG. 15 is a perspective view of the attachment member according to the first configuration example in a case in which the attachment member is viewed from an angle different from an angle in FIG. 14.
Figure 16:
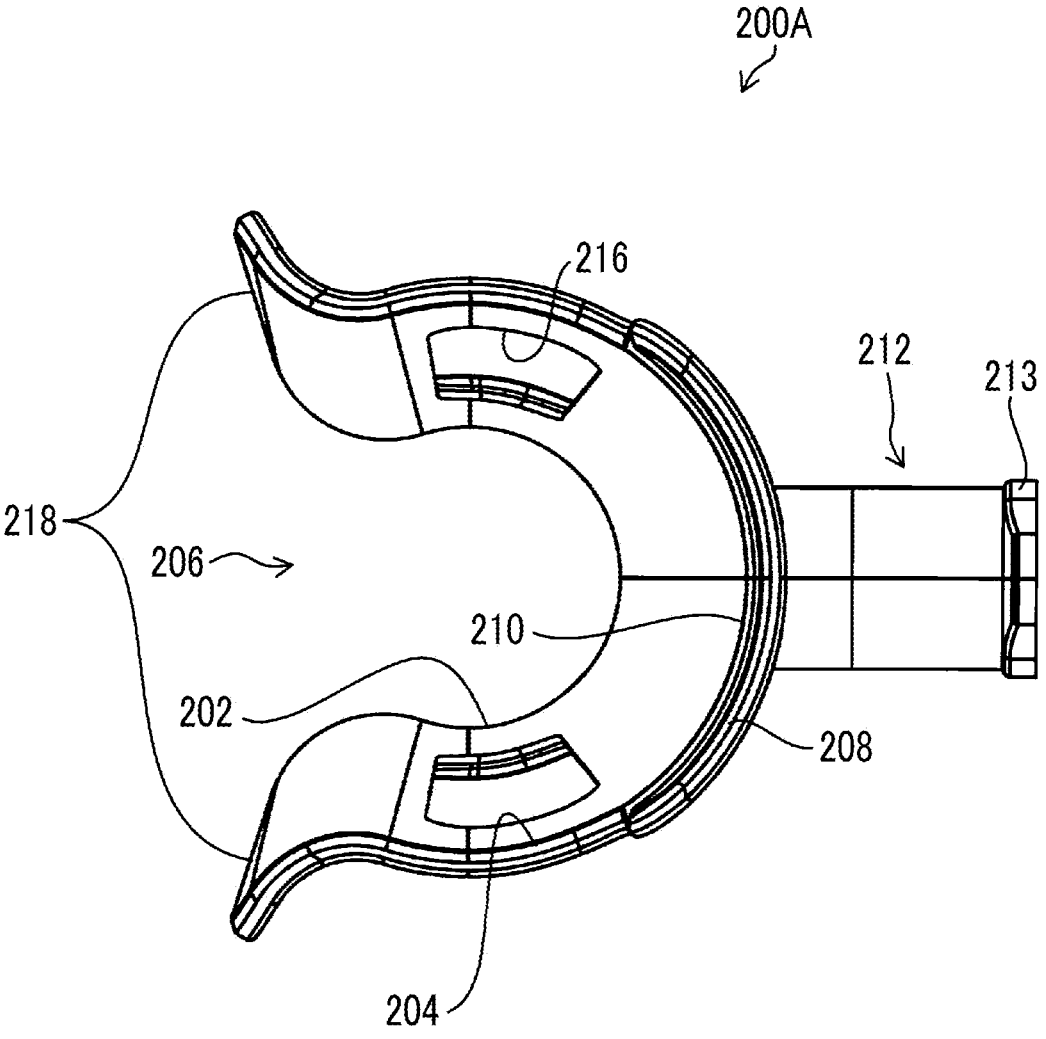
FIG. 16 is a top view of the attachment member according to the first configuration example.
Figure 17:
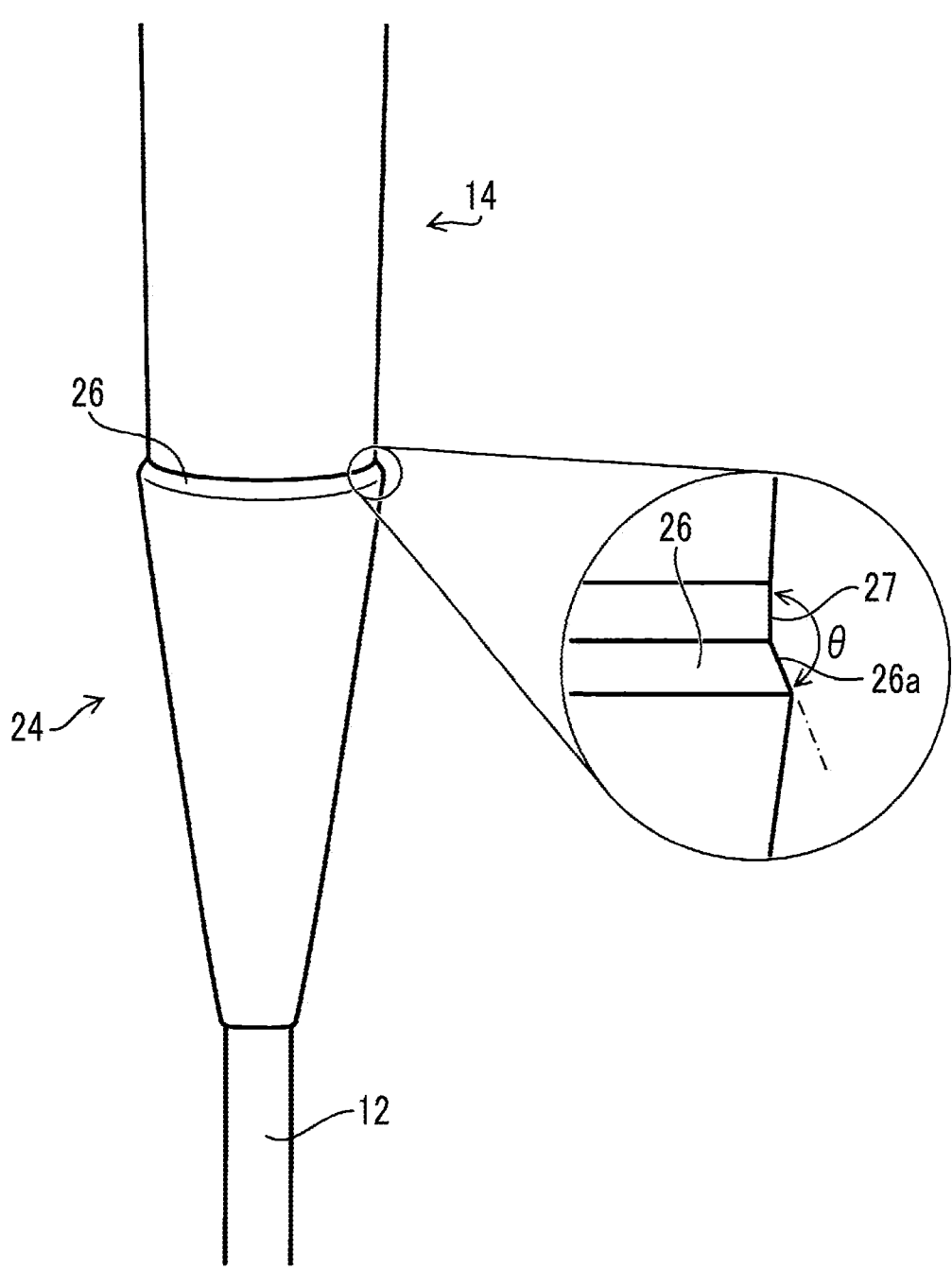
FIG. 17 is a main part configuration diagram showing a main part (peripheral part of a diameter-reduced part) of an operation part of an endoscope.

FIG. 14 is a perspective view of the attachment member 200A according to the first configuration example. FIG. 15 is a perspective view of the attachment member 200A according to the first configuration example in a case in which the attachment member 200A is viewed from an angle different from an angle in FIG. 14. FIG. 16 is a top view of the attachment member 200A according to the first configuration example. FIG. 17 is a main part configuration diagram showing a main part (peripheral part of the diameter-reduced part 24) of the operation part 14 of the endoscope 10.

As shown in FIGS. 14 to 16, the attachment member 200A according to the first configuration example has an overall shape based on a conical cylindrical shape whose diameter decreases toward a distal end side (lower side in FIG. 14). The attachment member 200A has a distal end opening 202 provided on the distal end side and a base end opening 204 provided on a base end side.

An insertion slit 206 for allowing the diameter-reduced part 24 of the operation part 14 to pass therethrough is provided in a side surface of the attachment member 200A. The insertion slit 206 is provided to extend along an axial direction of the attachment member 200A from the distal end opening 202 to the base end opening 204. An opening width of the insertion slit 206 is configured to be slightly smaller than an outer diameter of the diameter-reduced part 24 of the operation part 14, and the diameter-reduced part 24 of the operation part 14 can pass through the insertion slit 206 by expansion and contraction of the opening width of the insertion slit 206 due to elastic deformation of the attachment member 200A.

A protruding portion 208 that protrudes further toward the base end side than other portions is provided on the base end side of the attachment member 200A over a partial circumferential range (less than 180 degrees). The protruding portion 208 has a shape that forms a part of the outer peripheral surface of a conical cylindrical shape, similarly to the other portions of the attachment member 200A. A misalignment prevention portion 210 that is formed in a convex shape inward in a circumferential direction is provided on an inner surface of the protruding portion 208.

Meanwhile, as shown in FIG. 17, a stepped portion 26 having a protruding shape is provided in a portion of the operation part 14 on the base end side of the diameter-reduced part 24. The stepped portion 26 is provided in an annular shape along a circumferential direction of a side surface of the diameter-reduced part 24. In addition, the stepped portion 26 is formed to widen in an obtuse angle toward the distal end side. In other words, an angle θ of an inclined surface 26a of the stepped portion 26 with respect to a base end side adjacent surface 27 adjacent to a base end side of the stepped portion 26 is configured to be an obtuse angle that is larger than 90 degrees and smaller than 180 degrees.

The misalignment prevention portion 210 is a portion that engages with the stepped portion 26 configured as described above from the base end side in a case in which the attachment member 200A is mounted on the diameter-reduced part 24 of the operation part 14, and prevents the misalignment of the attachment member 200A with respect to the operation part 14 toward the distal end side.

The attachment member 200A is provided with a supply/discharge port 212. The other end part of the tube 300 is connected to the supply/discharge port 212. The supply/discharge port 212 is provided with a luer cap 213. The luer cap 213 has a tubular shape including a supply/discharge opening 214. The supply/discharge opening 214 communicates with the tube 300 via an internal pipe line (not shown) of the supply/discharge port 212. As a result, in a case in which the ultrasonic transmission medium is supplied from a syringe 310 (see FIG. 18) connected to the luer cap 213 of the supply/discharge port 212 to the supply/discharge opening 214, the ultrasonic transmission medium is sent to the balloon 110 through the tube 300, and the ultrasonic transmission medium is stored in the storage part 150 of the balloon 110. In addition, in a case in which suction is performed from the syringe 310, the ultrasonic transmission medium in the storage part 150 is discharged through the tube 300 and is collected in the syringe 310 via the supply/discharge opening 214.

Two opening windows 216 are provided on the outer peripheral surface of the attachment member 200A. The two opening windows 216 are formed to penetrate the side surface of the attachment member 200A. As a result, the operation part 14 (diameter-reduced part 24) can be visually recognized through the two opening windows 216. The two opening windows 216 need not be provided in the attachment member 200A.

The attachment member 200A comprises a pair of handhold portions 218 provided on both sides (both edges) of the insertion slit 206. The pair of handhold portions 218 are provided to be bent in a direction in which the handhold portions 218 are separated from each other toward the outside (direction spreading outward) (see FIG. 16). The pair of handhold portions 218 are portions provided to facilitate hooking of fingers of a hand of a user in a case in which the attachment member 200A is attached to and detached from the operation part 14, so that the opening width of the insertion slit 206 can be elastically expanded and contracted.

Figure 18:
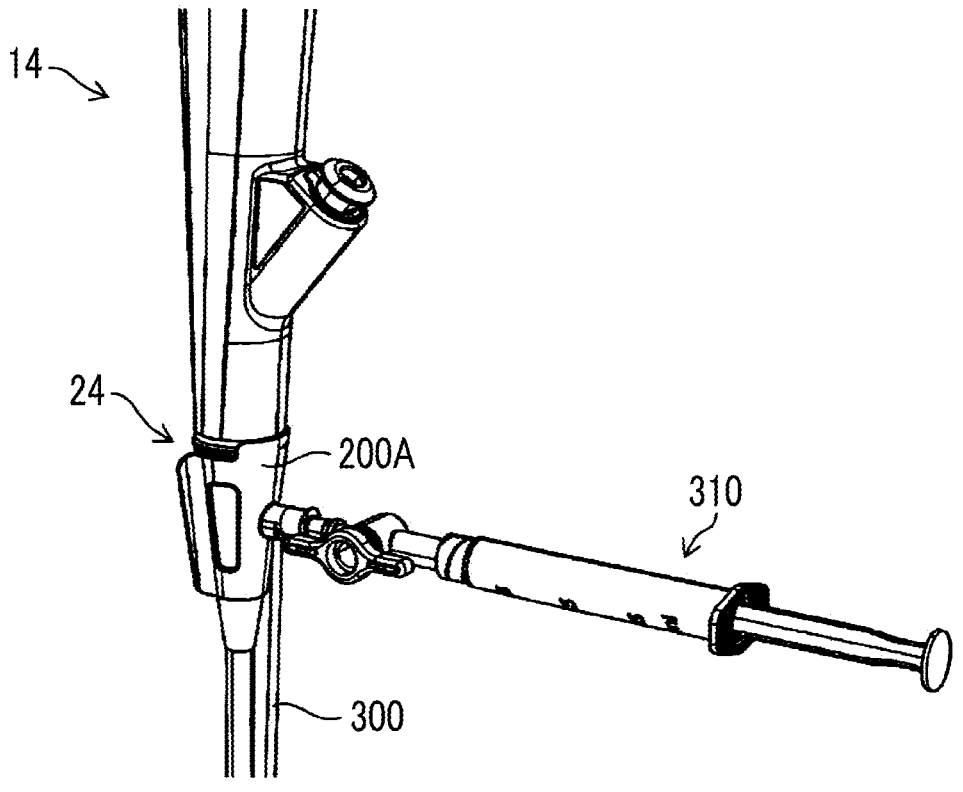
FIG. 18 is a perspective view showing a state in which the attachment member according to the first configuration example is mounted on the operation part of the endoscope.

FIG. 18 is a perspective view showing a state in which the attachment member 200A is mounted on the operation part 14 of the endoscope 10. In FIG. 18, reference numeral 310 indicates a syringe connected to the supply/discharge opening 214 of the supply/discharge port 212.

In a case in which the attachment member 200A is mounted on the operation part 14, the user hooks his or her fingers onto the pair of handhold portions 218 of the attachment member 200A to elastically widen the opening width of the insertion slit 206, so that the diameter-reduced part 24 of the operation part 14 can pass through the insertion slit 206. As a result, as shown in FIG. 18, the attachment member 200A can be easily mounted on the operation part 14.

In addition, in a state in which the attachment member 200A is mounted on the operation part 14, the misalignment prevention portion 210 is engaged with the stepped portion 26 provided on the operation part 14, so that the attachment member 200A can be prevented from being misaligned with respect to the operation part 14 toward the distal end side.

In a case in which the attachment member 200A is detached from the operation part 14, as in the case of the attachment, the user hooks his or her fingers onto the pair of handhold portions 218 of the attachment member 200A to elastically widen the opening width of the insertion slit 206, so that the attachment member 200A can be easily removed from the operation part 14 via the insertion slit 206.

Second Configuration Example

Figure 19:
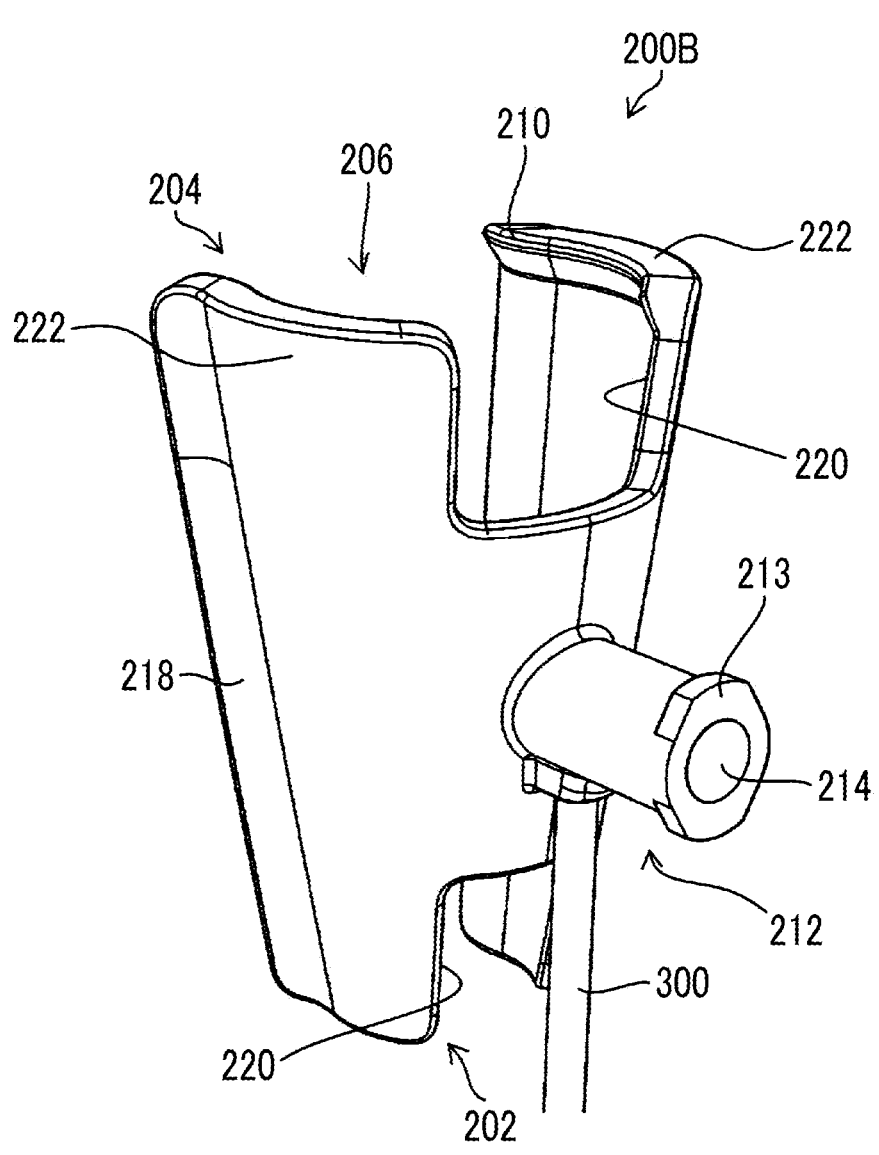
FIG. 19 is a perspective view of an attachment member according to a second configuration example.
Figure 20:
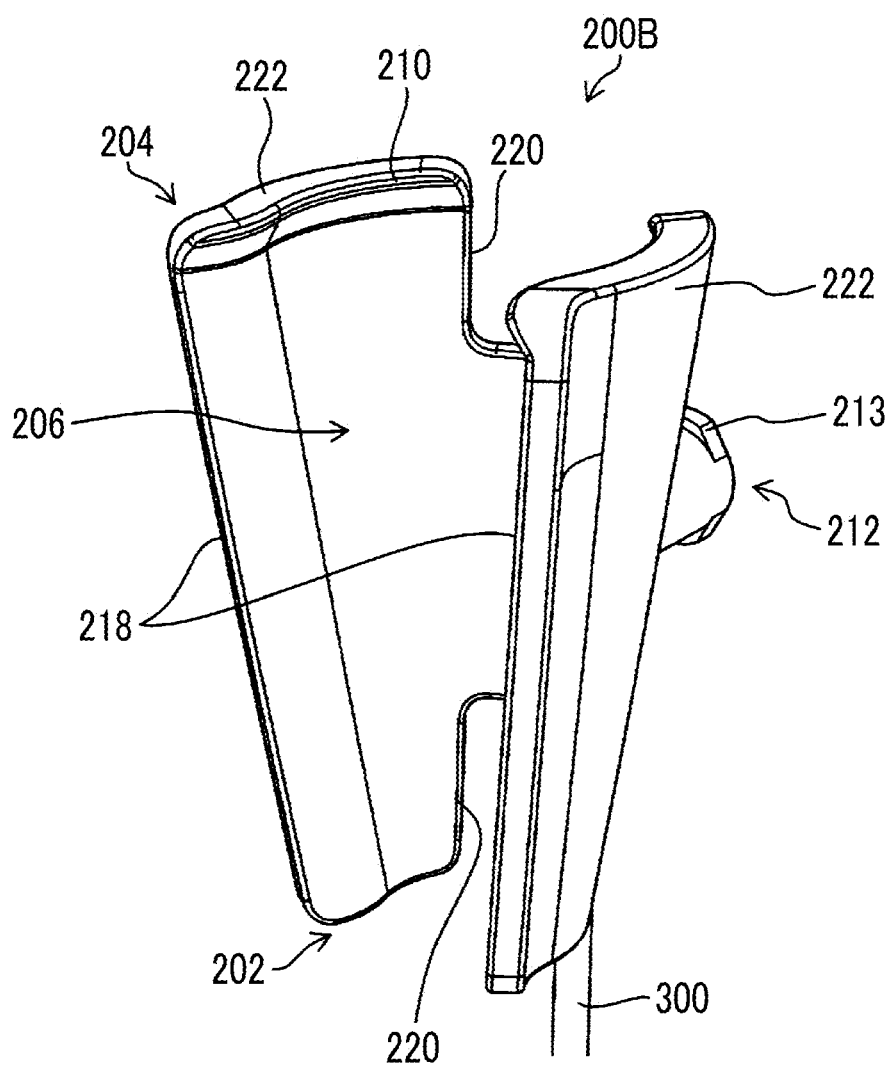
FIG. 20 is a perspective view of the attachment member according to the second configuration example in a case in which the attachment member is viewed from an angle different from an angle in FIG. 19.
Figure 21:
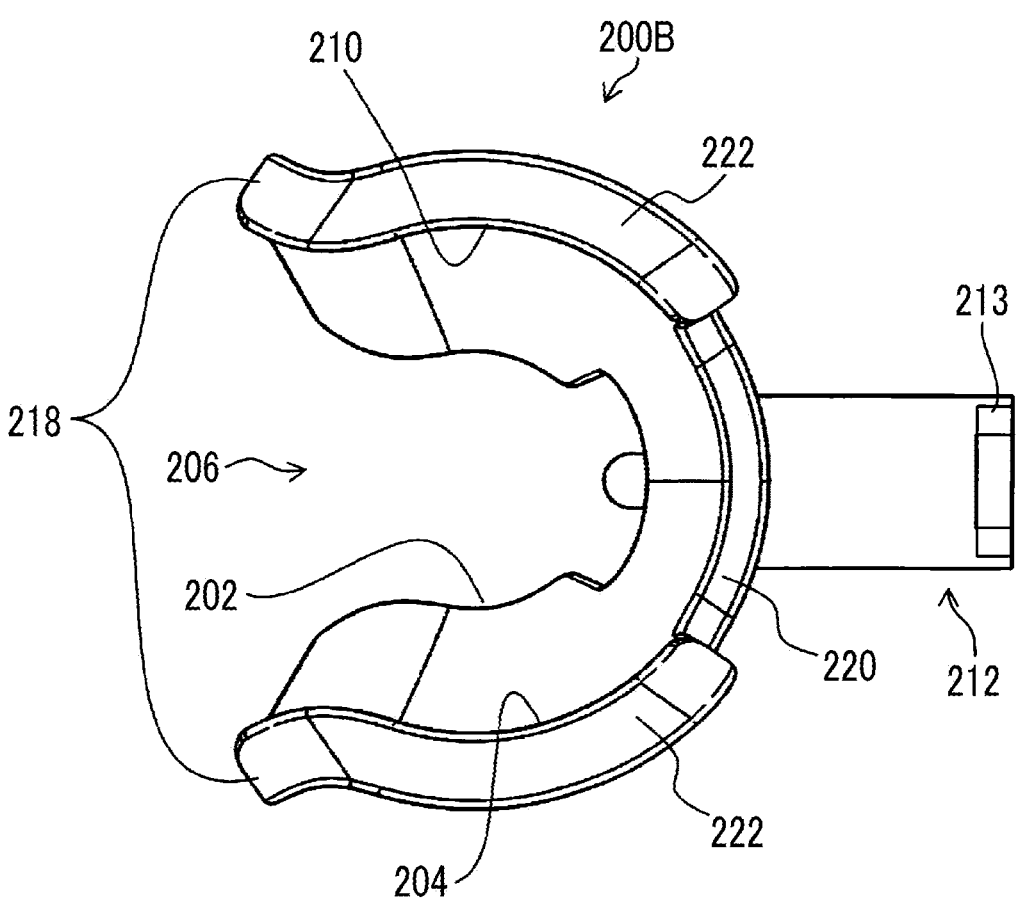
FIG. 21 is a top view of the attachment member according to the second configuration example.

FIG. 19 is a perspective view of the attachment member 200B according to the second configuration example. FIG. 20 is a perspective view of the attachment member 200B according to the second configuration example in a case in which the attachment member 200B is viewed from an angle different from an angle in FIG. 19. FIG. 21 is a top view of the attachment member 200B according to the second configuration example. In FIGS. 19 to 21, members common to the attachment member 200A according to the first configuration example are denoted by the same reference numerals.

As shown in FIGS. 19 to 21, similarly to the attachment member 200A according to the first configuration example, the attachment member 200B according to the second configuration example has an overall shape based on a conical cylindrical shape whose diameter decreases toward the distal end side (lower side in FIG. 19), and comprises the distal end opening 202, the base end opening 204, the insertion slit 206, the misalignment prevention portion 210, the supply/discharge port 212 (including the supply/discharge opening 214), and the pair of handhold portions 218. Since configurations of the respective parts of the attachment member 200B are common to those of the attachment member 200A, only different parts will be described, and description of the rest will be omitted.

The attachment member 200B has a substantially H-shaped shape that is open on the distal end side and the base end side, in a case in which the attachment member 200B is viewed in an axial direction of the supply/discharge opening 214. That is, the attachment member 200B has a pair of groove portions 220, each of which being formed by cutting a part of an outer peripheral surface of a conical cylinder shape into a rectangular shape, on the distal end side and the base end side, and the groove portions 220 are open to the distal end opening 202 and the base end opening 204.

The attachment member 200B comprises a pair of base end wall surface portions 222 constituting the base end opening 204. The pair of base end wall surface portions 222 are provided at positions sandwiched between the groove portion 220 and the insertion slit 206 on the base end side, and are provided at positions facing each other.

The misalignment prevention portion 210 that is formed in a convex shape inward in the circumferential direction is provided on an inner surface of each base end wall surface portion 222. That is, the attachment member 200B is provided with the misalignment prevention portion 210 at two inner side positions of the base end opening 204.

Figure 22:
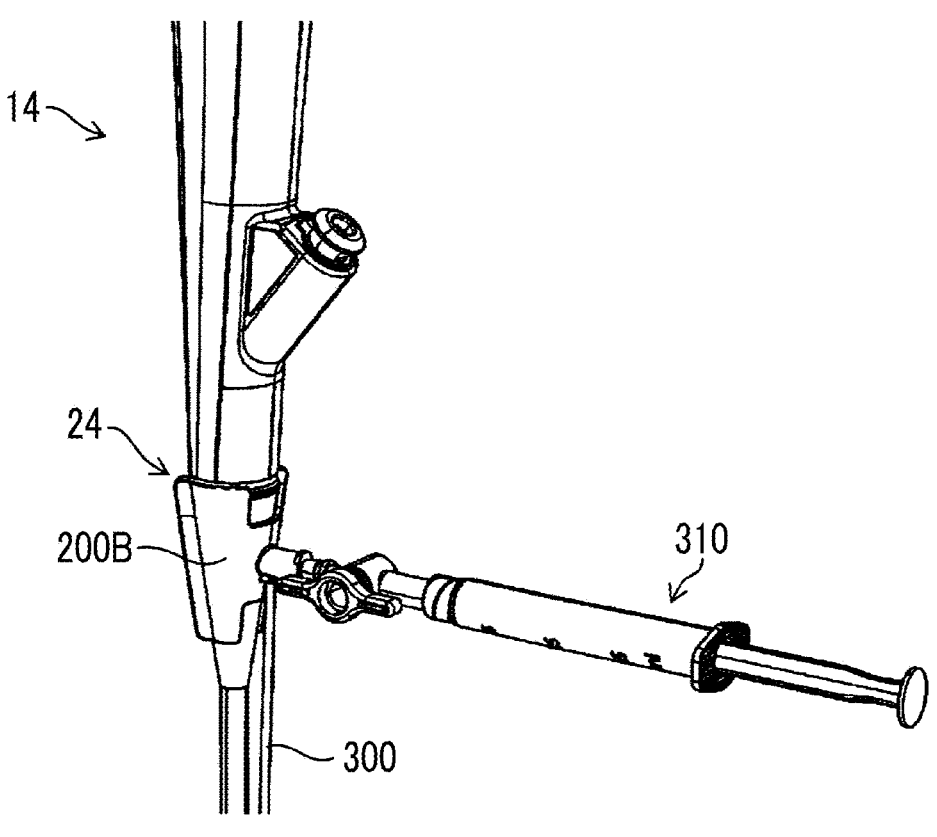
FIG. 22 is a perspective view showing a state in which the attachment member according to the second modification example is mounted on the operation part of the endoscope.

FIG. 22 is a perspective view showing a state in which the attachment member 200B is mounted on the operation part 14 of the endoscope 10. As shown in FIG. 22, the attachment member 200B is mounted on the diameter-reduced part 24 in the operation part 14 of the endoscope 10.

Similarly to the attachment member 200A according to the first configuration example, the attachment member 200B according to the second configuration example comprises the pair of the handhold portions 218 on both sides of the insertion slit 206, so that the attachment and detachment (mounting and detachment) of the attachment member 200B with respect to the operation part 14 can be easily performed. In addition, the misalignment prevention portion 210 can prevent the attachment member 200B from being misaligned on the distal end side after the attachment member 200B is mounted on the operation part 14.

In the above-described embodiment, the stepped portion 26 having a protruding shape is provided in a portion on the base end side of the diameter-reduced part 24 in order to engage the misalignment prevention portion 210 of the attachment member 200 (200A, 200B) with the operation part 14, but the present invention is not limited to this. For example, a groove portion in the circumferential direction may be provided in the diameter-reduced part 24, and the misalignment prevention portion 210 may be engaged with the groove portion.

Although the embodiment of the present invention has been hitherto described, the present invention is not limited to the above-mentioned examples, and various improvements and modifications may be made without departing from the scope of the present invention.

EXPLANATION OF REFERENCES

10: endoscope
12: endoscope insertion part
14: operation part
16: universal cord
18: angle lever
20: suction button
22: treatment tool inlet port
24: diameter-reduced part
26: stepped portion
26a: inclined surface
27: base end side adjacent surface
30: distal end part body
32: bendable part
34: soft part
36: longitudinal axis
40: ultrasonic attachment part
42: outlet port forming part
44: body part
50: ultrasonic transducer
52: transducer surface
53: signal cable
54: standing wall part
56: opening forming surface
58: treatment tool outlet port
60: pipe line
62: treatment tool insertion channel
64: observation optical system
64a: observation window
64b: lens system
64c: imaging element
66: illumination optical system
66a: illumination window
68: optical system housing part
70: convex surface
72: stepped surface
74: signal cable
76: light guide
90: puncture needle
100: balloon unit
110: balloon
112: longitudinal axis
120: cover body
122: connecting body
124: fixing body
126: opening portion
128: cover body space portion
130: outer part

132: inner part
134: left side surface portion
135: right side surface portion
136: inclined surface portion
137: bottom surface portion
138: outer opening portion
139: outer space portion
140: groove portion
142: integrally formed object
144: left side surface portion
145: right side surface portion
146: inclined surface portion
147: bottom surface portion
148: inner opening portion
149: inner space portion
150: storage part
152: communication path
154: bulging portion
156: through-passage
158: fixing surface
160: left side surface portion
162: right side surface portion
164: bottom surface portion
166: open window
168: connecting body space portion
170: thick portion
172: inclined surface
174: tube connection port
200: attachment member
200A: attachment member
200B: attachment member
202: distal end opening
204: base end opening
206: insertion slit
208: protruding portion
210: misalignment prevention portion
212: supply/discharge port
213: luer cap
214: supply/discharge opening
216: opening window
218: handhold portion
220: groove portion
222: base end wall surface portion
300: tube
310: syringe

What is claimed is:

1. An endoscope balloon that covers an ultrasonic transducer provided in a distal end part body of an endoscope insertion part, the endoscope balloon configured separately from the distal end part body, the endoscope balloon comprising:

a cover body that has a shape which is closed on a distal end side in a first direction corresponding to a longitudinal direction of the endoscope insertion part and has an opening on a base end side in the first direction, includes a bulging portion configured to bulge by storing an ultrasonic transmission medium, and is mounted on the distal end part body and is configured to cover the ultrasonic transducer;

a fixing body that is provided on the base end side with respect to the cover body and that is fixed to a fixed part of the endoscope insertion part; and a connecting body that connects the cover body and the fixing body, and has an open window that is configured to be at a position corresponding to a treatment tool outlet port provided in the distal end part body, wherein the fixing body has a tubular shape configured to allow the distal end part body of the endoscope to be removably inserted, and the fixing body is configured to be disposed on the base end side of the treatment tool outlet port in the first direction.

2. The endoscope balloon according to claim 1, wherein the fixing body is closely fixed to the fixed part.

3. The endoscope balloon according to claim 1, wherein the fixing body is configured of a tubular body having a through-passage in the first direction, and an inner peripheral surface of the tubular body is fixed to the fixed part.

4. The endoscope balloon according to claim 3, wherein the opening of the cover body is provided at a position intersecting an extension direction of an axis of the through-passage.

5. The endoscope balloon according to claim 1, wherein the fixing body is fixed to the distal end part body as the fixed part.

6. The endoscope balloon according to claim 1, wherein the fixing body is configured to be fixed to a bendable part provided on the base end side of the distal end part body of the endoscope insertion part.

7. The endoscope balloon according to claim 1, wherein the cover body has a cover body fixing portion that is configured to be fixed to the distal end part body.

8. The endoscope balloon according to claim 7, wherein the cover body fixing portion has a pair of fixing surfaces facing each other in a second direction orthogonal to the first direction, and the pair of fixing surfaces are configured to elastically hold the distal end part body.

9. The endoscope balloon according to claim 1, wherein the connecting body has a gutter shape that is configured to be open on a side where the treatment tool outlet port is provided.

10. The endoscope balloon according to claim 1, wherein the cover body has an inner part, an outer part that covers the inner part, and a storage part that stores the ultrasonic transmission medium between the inner part and the outer part, and the outer part has the bulging portion at a position configured to face a transducer surface of the ultrasonic transducer.

11. The endoscope balloon according to claim 10, wherein the inner part, the connecting body, and the fixing body are integrally formed.

12. The endoscope balloon according to claim 10, wherein the connecting body has a communication port that communicates with the storage part.

13. An endoscope balloon unit comprising:

the endoscope balloon according to claim 1;

an attachment member that is configured to be attachable to and detachable from an operation part connected to the base end side of the endoscope insertion part and has a supply/discharge port for supplying and discharging the ultrasonic transmission medium; and a pipe line member that sends the ultrasonic transmission medium between the attachment member and the endoscope balloon.

14. An endoscope mounted with the endoscope balloon unit according to claim 13.

\* \* \* \* \*